US009414742B2

(12) United States Patent
Sato

(10) Patent No.: US 9,414,742 B2
(45) Date of Patent: Aug. 16, 2016

(54) ENDOSCOPE CONNECTION INSTRUMENT AND ENDOSCOPE CLEANING/DISINFECTING APPARATUS

(71) Applicant: OLYMPUS CORPORATION, Tokyo (JP)

(72) Inventor: Norito Sato, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/635,054

(22) Filed: Mar. 2, 2015

(65) Prior Publication Data

US 2015/0173597 A1 Jun. 25, 2015

Related U.S. Application Data

(63) Continuation of application No. PCT/JP2014/062423, filed on May 9, 2014.

(30) Foreign Application Priority Data

Jul. 3, 2013 (JP) .................................. 2013-139889

(51) Int. Cl.
*A61B 1/00* (2006.01)
*A61B 1/12* (2006.01)
*G02B 23/24* (2006.01)

(52) U.S. Cl.
CPC .............. *A61B 1/123* (2013.01); *A61B 1/00128* (2013.01); *A61B 1/12* (2013.01); *G02B 23/2476* (2013.01); *Y10T 137/9029* (2015.04)

(58) Field of Classification Search
CPC .......... A61B 1/12; A61B 1/121; A61B 1/123; A61B 1/125; A61B 1/126; A61B 1/00112; A61B 1/00121; A61B 1/00128; B08B 9/00; B08B 9/021; B08B 9/023; B08B 9/027; B08B 9/032; B08B 9/0321
See application file for complete search history.

(56) References Cited

U.S. PATENT DOCUMENTS

| 2006/0269442 A1* | 11/2006 | Nguyen ................. A61B 1/125 422/28 |
| 2007/0185385 A1 | 8/2007 | Noguchi et al. |
| 2010/0004510 A1 | 1/2010 | Kuroshima |

FOREIGN PATENT DOCUMENTS

| EP | 1767140 A1 | 3/2007 |
| JP | 10-234666 A | 9/1998 |
| JP | 2003-116789 A | 4/2003 |

(Continued)

OTHER PUBLICATIONS

Japanese Office Action dated Sep. 2, 2014 issued in JP 2014-532143.

*Primary Examiner* — David Cormier
(74) *Attorney, Agent, or Firm* — Scully, Scott, Murphy & Presser, PC

(57) ABSTRACT

A fitting pressing member includes: a first opening that opens inside a fitting of an endoscope; a second opening that is communicably connected to the first opening and is connectable to a fluid supply source; a cylindrical portion formed from the first opening to a predetermined position, the cylindrical portion covering a part of a hollow portion communicably connected to the first opening and the second opening; a narrowing portion including a side face whose outer diameter increases from the predetermined position toward the second opening, the narrowing portion covering the other part of the hollow portion; and a plurality of grooves formed over a predetermined area from the predetermined position in an outer surface of the narrowing portion.

12 Claims, 19 Drawing Sheets

(56) References Cited

FOREIGN PATENT DOCUMENTS

| JP | 2006-006565 A | 1/2006 |
| JP | 2010-011977 A | 1/2010 |
| JP | 2012-040240 A | 3/2012 |
| WO | WO 2006/001336 A1 | 1/2006 |

* cited by examiner

ENDOSCOPE CONNECTION INSTRUMENT AND ENDOSCOPE CLEANING/DISINFECTING APPARATUS

CROSS REFERENCE TO RELATED APPLICATION

This application is a continuation application of PCT/JP2014/062423 filed on May 9, 2014 and claims benefit of Japanese Application No. 2013-139889 filed in Japan on Jul. 3, 2013, the entire contents of which are incorporated herein by this reference.

BACKGROUND OF INVENTION

1. Field of the Invention

The present invention relates to an endoscope connection instrument and an endoscope cleaning/disinfecting apparatus, and specifically relates to an endoscope connection instrument to be connected to an endoscope fitting and an endoscope cleaning/disinfecting apparatus.

2. Description of the Related Art

Conventionally, endoscopes are widely used for examinations and treatments of insides of bodies. Since endoscopes are each inserted into a body, the endoscopes are cleaned after use. Therefore, endoscope cleaning apparatuses for cleansing endoscopes are also widely used.

In endoscope cleaning using an endoscope cleaning apparatus, not only surfaces of the endoscope but also the inside of each of ducts provided inside is cleaned. Thus, fittings communicably connected to respective ducts inside the endoscope and the endoscope cleaning apparatus (hereinafter also simply referred to as "cleaning apparatus") are connected via cleaning tubes, and, e.g., a cleaning liquid, a disinfectant liquid or a rinsing liquid sent from the cleaning apparatus is sent into the respective ducts of the endoscope, whereby the inside of each of the ducts is cleaned and disinfected. Since a connection part between each cleaning tube and the corresponding fitting remains in a close contact state even though some kind of load is imposed on the connection part and the inside of the corresponding duct is hermetically sealed, the flow rate less changes, ensuring a stable capability of cleaning the inside of the duct, and also enabling detection of the cleaning tube coming off from the fitting based on a flow rate change.

Furthermore, various measures for cleaning and disinfecting an outer surface of a connection fitting of an endoscope to which a cleaning tube is connected have been proposed. For example, Japanese Patent Application Laid-Open Publication No. 10-234666 proposes a suction duct cleaning instrument in which a cover barrel that surrounds a periphery of a suction tube connection fitting is provided and a cleaning liquid outflow hole for allowing a cleaning liquid to flow out is provided in the cover barrel.

Also, Japanese Patent Application Laid-Open Publication No. 2012-40240 discloses a cleaning adapter for an endoscope, and discloses a structure in which a seal member is brought into close contact with an upper face of a valve casing.

SUMMARY OF THE INVENTION

An endoscope connection instrument according to an aspect of the present invention which is to be connected to an endoscope fitting, the endoscope connection instrument comprising: a first opening having a predetermined outer diameter in order to open inside the endoscope fitting when the endoscope connection instrument is connected to the endoscope fitting; a second opening that is communicably connected to the first opening, is arranged on a fluid supply source side relative to the first opening, and allows a fluid from the fluid supply source to flow thereinto via a cleaning tube; a hollow portion that is an internal space communicably connected to the first opening and the second opening; a cylindrical portion to be inserted into the endoscope fitting, the cylindrical portion covering a part from the first opening to a predetermined position of the hollow portion; a narrowing portion to be inserted into the endoscope fitting, the narrowing portion including a side face whose outer diameter increases over a predetermined distance from the predetermined position toward the second opening, and covering the hollow portion; and a plurality of grooves formed over a predetermined area from the predetermined position in an outer surface of the narrowing portion.

An endoscope cleaning/disinfecting apparatus according to one aspect of the present invention includes: the endoscope connection instrument of the present invention connected to the endoscope cleaning/disinfecting apparatus via the cleaning tube.

DETAILED DESCRIPTION OF THE PREFERRED EMBODIMENT(S)

Figure 1:
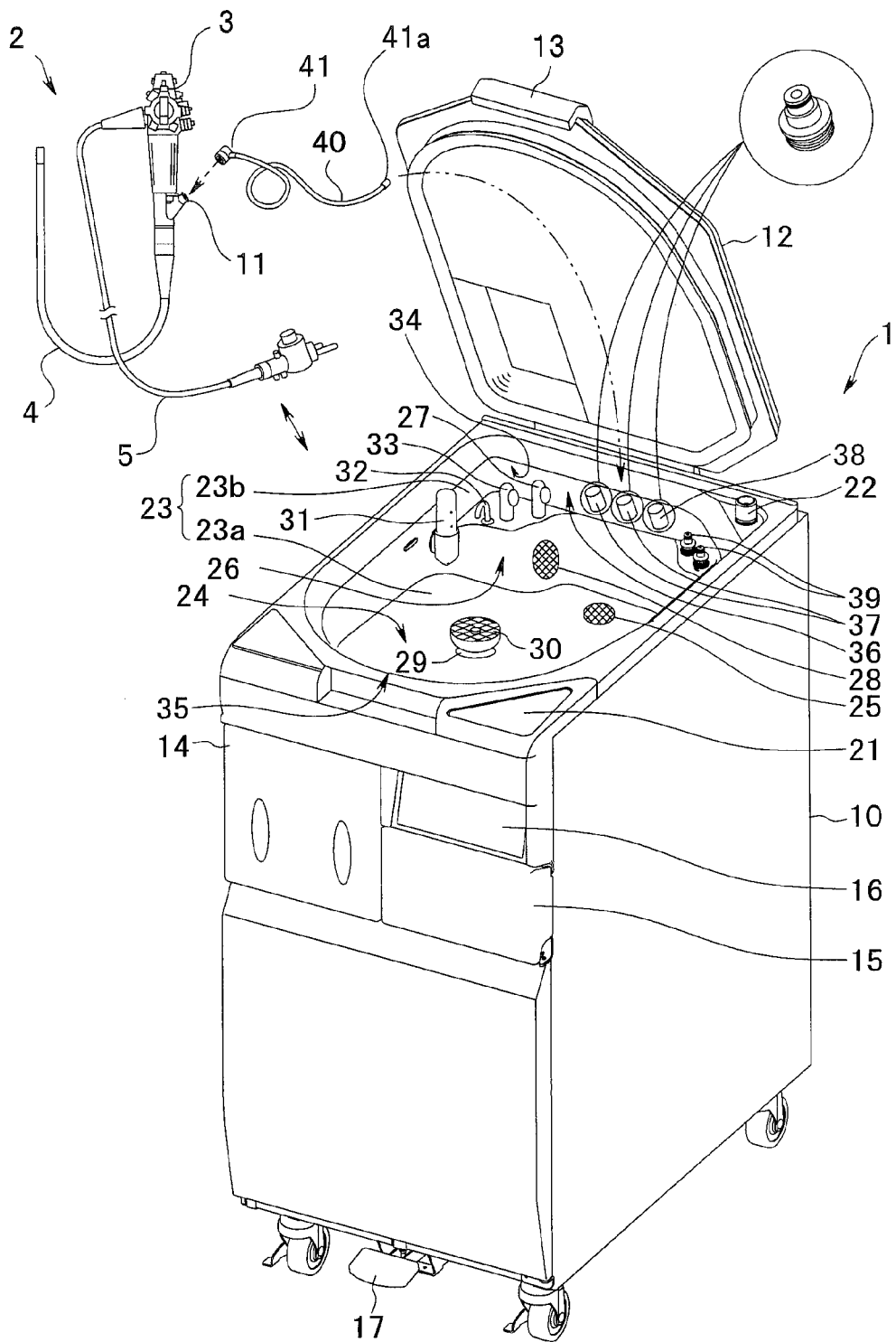
FIG. 1 is a perspective view of an endoscope cleaning/disinfecting apparatus according to a first embodiment of the present invention, in which a top cover is opened, allowing an endoscope to be received in a cleaning/disinfecting bath.

Embodiments of the present invention will be described below with reference to the drawings.

Note that in each of the drawings used for the below description, components are illustrated on difference scales so that the respective components have sizes that are large enough to be recognized in the drawing, and the present invention is not limited only to the counts and amounts, and the shapes of the components, and the size ratios and the relative positional relationships among the components illustrated in the drawings.

First Embodiment

Overall Configuration of Cleaning/Disinfecting Apparatus

FIG. 1 is a perspective view of an endoscope cleaning/disinfecting apparatus in a state in which a top cover is opened, allowing an endoscope to be received in a cleaning/disinfecting bath.

As illustrated in FIG. 1, an endoscope cleaning/disinfecting apparatus 1 is an apparatus for cleaning/disinfecting a used endoscope 2, and a main portion of the endoscope cleaning/disinfecting apparatus 1 includes an apparatus body 10, and on an upper portion thereof, a top cover 12, which is a lid body connected to the apparatus body 10 via, for example, a non-illustrated hinge so as to be openable and closable.

The endoscope 2 includes an operation portion 3, an elongated insertion portion 4 that has flexibility and extends from the operation portion 3, and a universal cable 5 to be connected to, e.g., a processor apparatus. At the operation portion 3, e.g., operation knobs and operation buttons are arranged.

The endoscope cleaning/disinfecting apparatus 1 is configured so that when the top cover 12 is closed on the apparatus body 10, the top cover 12 is secured to the apparatus body 10 via a latch 13.

In, for example, an upper portion of a left half portion of a front face in the figure (hereinafter referred to as "front face") of the apparatus body 10, which is close to an operator, a detergent/alcohol tray 14 is disposed in such a manner that the detergent/alcohol tray 14 can be drawn forward from the apparatus body 10. Also, in, for example, an upper portion of a right half portion of the front face of the apparatus body 10, a cassette tray 15 is disposed in such a manner that the cassette tray 15 can be drawn forward from the apparatus body 10.

Furthermore, in a portion above the cassette tray 15 in the front face of the apparatus body 10, a sub-operation panel 16 with, e.g., a cleaning/disinfecting time period display and an instruction button for heating the disinfectant liquid disposed thereon is disposed. Also, a pedal switch 17 for opening the top cover 12 closed on the upper portion of the apparatus body 10 upward from the apparatus body 10 by a stepping operation by the operator is disposed in a lower portion of the front face in the figure of the apparatus body 10.

Also, a main operation panel 21 with a start switch for cleaning/disinfecting operation of the apparatus body 10 and setting switches such as a cleaning/disinfecting mode selection switch disposed therein is provided, for example, close to opposite ends on the front face side of an upper face of the apparatus body 10, which is close to the operator.

Also, a water supply hose connection part 22 for supplying tap water to the apparatus body 10, to which a water supply hose connected to a tap water faucet is connected, is disposed on a side of the upper face of the apparatus body 10 that faces the front face close to the operator.

Furthermore, a cleaning/disinfecting bath 23 capable of receiving the endoscope 2 is provided in a roughly-center portion of the upper face of the apparatus body 10. The cleaning/disinfecting bath 23 includes a bath body 23a, and a terrace portion 23b continuously provided at an outer circumference of an endoscope receiving opening of the bath body 23a.

When a used endoscope 2 is cleaned/disinfected, the bath body 23a can receive the endoscope 2, and in a bottom face 24, which is a surface inside the bath of the bath body 23a, a drain port 25 for draining, e.g., a cleaning liquid, water, alcohol or a disinfectant liquid supplied to the bath body 23a, from the bath body 23a is provided. Also, at an arbitrary position in a circumferential side face 26, which is a surface inside the bath of the bath body 23a, a circulation port 28 for supplying the aforementioned liquid such as the cleaning liquid, the water, the alcohol or the disinfectant liquid supplied in the bath body 23a to the bath body 23a again is provided.

In the cleaning/disinfecting bath 23, a non-illustrated ultrasound transducer and a non-illustrated heater are disposed on the back face side of the bath body 23a and a duct disinfection port 29 and a cleaning case 30 are disposed in a rough center of the bottom face 24 of the bath body 23a. At an arbitrary position of the side face 26 of the bath body 23a, a water level sensor 31 for detecting, a level of, e.g., the cleaning liquid, the water, the alcohol or the disinfectant liquid supplied to the bath body 23a is provided.

In a face other than a terrace surface of the terrace portion 23b, a detergent nozzle 32 for supplying a cleaning agent to be diluted to obtain a predetermined concentration and a disinfectant liquid nozzle 33 for supplying a diluted and prepared disinfectant liquid are disposed. Furthermore, in the surface parallel to the bottom face 24 of the bath body 23a of the terrace portion 23b, a water supply circulation nozzle 27 is disposed.

Also, in a surface 36 on a side facing a position 35 of the terrace surface 34 of the terrace portion 23b, the position 35 being close to the operator, a plurality, here, two ports 37 for air/water feeding/forceps ports, which are fluid supply portions for supplying, e.g., a cleaning liquid, water, an alcohol, a disinfectant liquid or air to channels, which are endoscope ducts provided inside the endoscope 2, a forceps elevation port 38 and a leakage detection port 39 are disposed.

Also, the endoscope cleaning/disinfecting apparatus 1 according to the present embodiment has a flow control function that detects duct clogging inside the channels of the endoscope 2 during cleaning and disinfecting. Note that since a specific configuration and operation of the flow control function are techniques conventionally used, detailed description thereof will be omitted.

At opposite ends of a cleaning tube 40, respective connectors 41 and 41a are provided. In the endoscope 2, a fitting 11 communicably connected to a duct inside the endoscope 2 is provided. The connector 41 is an endoscope-side connector to be connected to the fitting 11 communicably connected to the duct inside the endoscope 2. The connector 41a is an apparatus-side connector to be connected to a port 37 for an air/water feeding/forceps port.

When the endoscope 2 is cleaned, a liquid such as a cleaning liquid supplied through the cleaning tube 40 is supplied from the connector 41 into the duct inside the endoscope 2 through fitting 11.

(Configuration of Connector 41)

Figure 2:
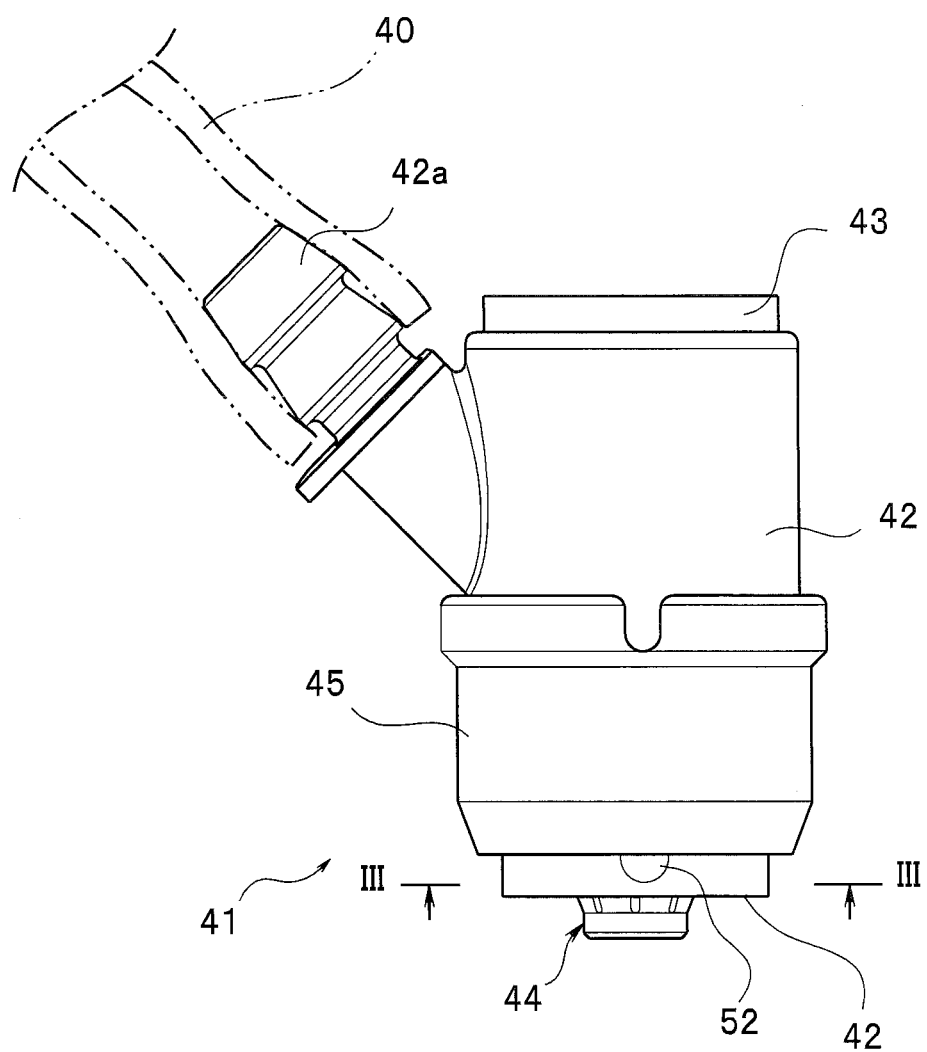
FIG. 2 is a front view of a connector 41 according to the first embodiment of the present invention.
Figure 3:
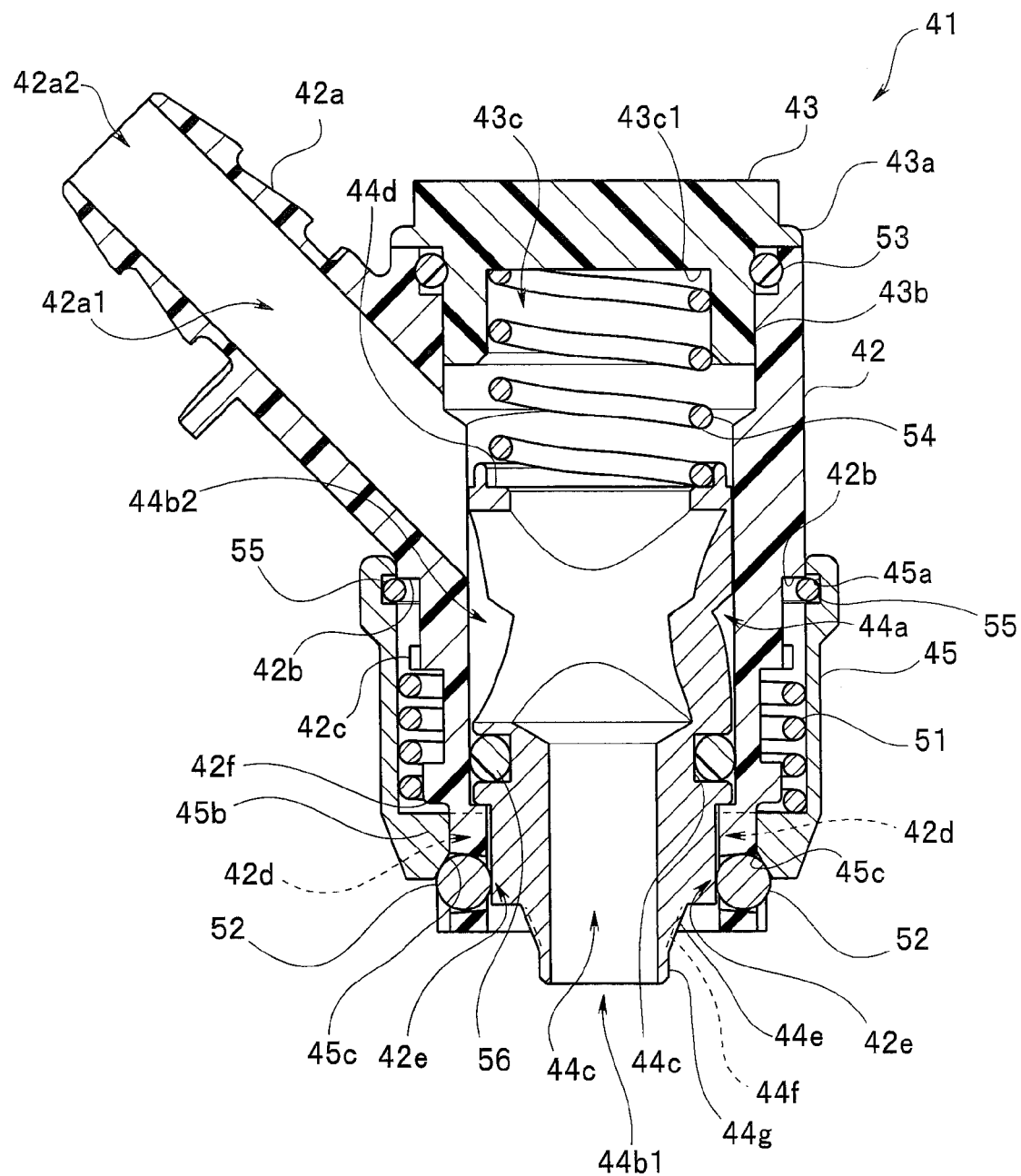
FIG. 3 is a cross-sectional view of the connector 41 along line III-III in FIG. 2.
Figure 4:
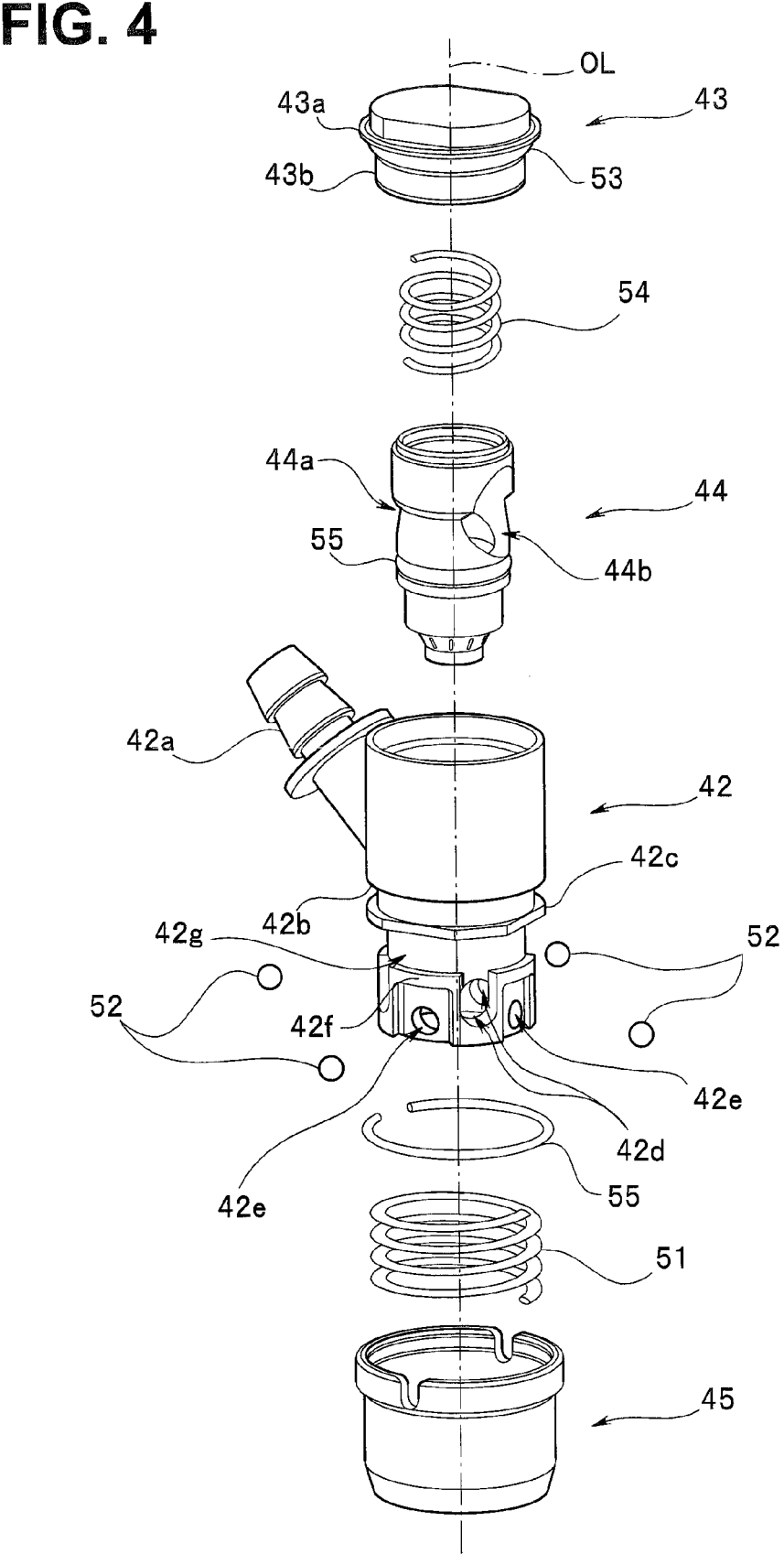
FIG. 4 is an exploded and assembly view of the connector 41 according to the first embodiment of the present invention.

Next, a configuration of the connector 41, which is an endoscope-side connector, will be described. FIG. 2 is a front view of the connector 41. FIG. 3 is a cross-sectional view of the connector 41 along line III-III in FIG. 2. FIG. 4 is an exploded and assembly view of the connector 41.

The connector 41 includes a body 42, a lid member 43, a fitting pressing member 44 and a cover member 45.

The body 42 is a resin cylindrical member, and includes a tube connection portion 42a that protrudes obliquely upward from a side face of an upper portion of the cylindrical member. The tube connection portion 42a includes a step portion at an outer circumferential face, and a resin cleaning tube 40 is put on and thereby connected to the tube connection portion 42a. The tube connection portion 42a includes a second opening, and the second opening 42a2 is communicably connected to a later-described first opening 44b1 via a later-described hollow portion 44b3. In other words, a fluid supplied from a fluid supply source can be introduced from the second opening and discharged from the first opening.

At an outer circumferential portion of a center portion of the body 42, a step portion 42b is formed along a circumferential direction. Below the step portion 42b, a circumferential projection portion 42c is formed along the circumferential direction. As described later, an end of the spring 51 abuts the projection portion 42c. Below the projection portion 42c, a plurality of (here, four) holes 42d are provided.

Also, in a lower portion of the body 42, a plurality of (here, four) holes 42e are formed in the circumferential direction.

An inner circumferential face of each hole 42e is an inclined surface whose inner diameter decreases from the outside toward the inside. As described later, each hole 42e receives a metal ball 52 from the outside, and each ball 52 catches on the tapered surface of the corresponding hole 42e, preventing the ball 52 from falling off to the inside of the body 42. Each of the holes 42d and 42e is an opening portion that brings the inside and the outside of a thin wall portion of the body 42, which is a cylindrical body, into communication with each other.

In the peripheries of the respective holes 42d, a protrusion portion 42f is formed so as to surround the respective holes 42d. Furthermore, as described later, a space 42g that allows a fluid to flow thereinto is formed between the step portion 42b and the protrusion portion 42f.

The resin lid member 43 is attached to an upper portion of the body 42. The lid member 43 includes a ring-shaped protrusion portion 43a having an outer diameter that is the same as an outer diameter of the upper portion of the body 42. At a lower portion of the lid member 43, an extension portion 43b that extends downward is provided, and an O-shaped ring 53 is attached to the extension portion 43b. The O-shaped ring 53 hermetically seals the inside of the body 42 when the lid member 43 is attached to the upper portion of the body 42.

Also, the extension portion 43b includes a recess portion 43c that opens downward. A spring 54 is provided inside the recess portion 43c, an upper end of the spring 54 abuts a bottom face 43c1 of the recess portion 43c, and a lower end of the spring 54 abuts an upper portion of the later-described fitting pressing member 44. The spring 54 is provided in a compressed state between the lid member 43 and the fitting pressing member 44.

The fitting pressing member 44 is made of a metal such as a stainless steel and has a circular cylindrical shape. A configuration of the fitting pressing member 44, which is an endoscope connection instrument, will be described later.

The cover member 45 is fitted on and thereby attached to the lower portion of the body 42. The cover member 45 is made of a metal such as a stainless steel and has a circular cylindrical shape, and in an upper portion of an inner circumferential face of the cover member 45, an inner circumferential groove 45a is formed along the circumferential direction. In the inner circumferential groove 45a, a C-shaped ring 55 made of a metal such as a stainless steel is fitted in the inner circumferential groove in such a manner that the C-shaped ring 55 is compressed inward in a radial direction.

The C-shaped ring 55 fitted in the inner circumferential groove 45a butts the step portion 42b of the body 42, restricting the cover member 45 from moving to an upper position in the body 42.

The cover member 45 includes an inward flange portion 45b at a lower portion. A spring 51 is disposed inside the cover member 45, and a lower end portion of the spring 51 abuts the inward flange portion 45b, and an upper end portion of the spring 51 abuts the projection portion 42c of the body 42. The spring 51 is disposed between the inward flange portion 45b and the projection portion 42c. Also, at a lower portion of an inner circumferential face of the cover member 45, a tapered portion 45c is formed.

The fitting pressing member 44, which is an endoscope connection instrument, is disposed inside the body 42.

Figure 5:
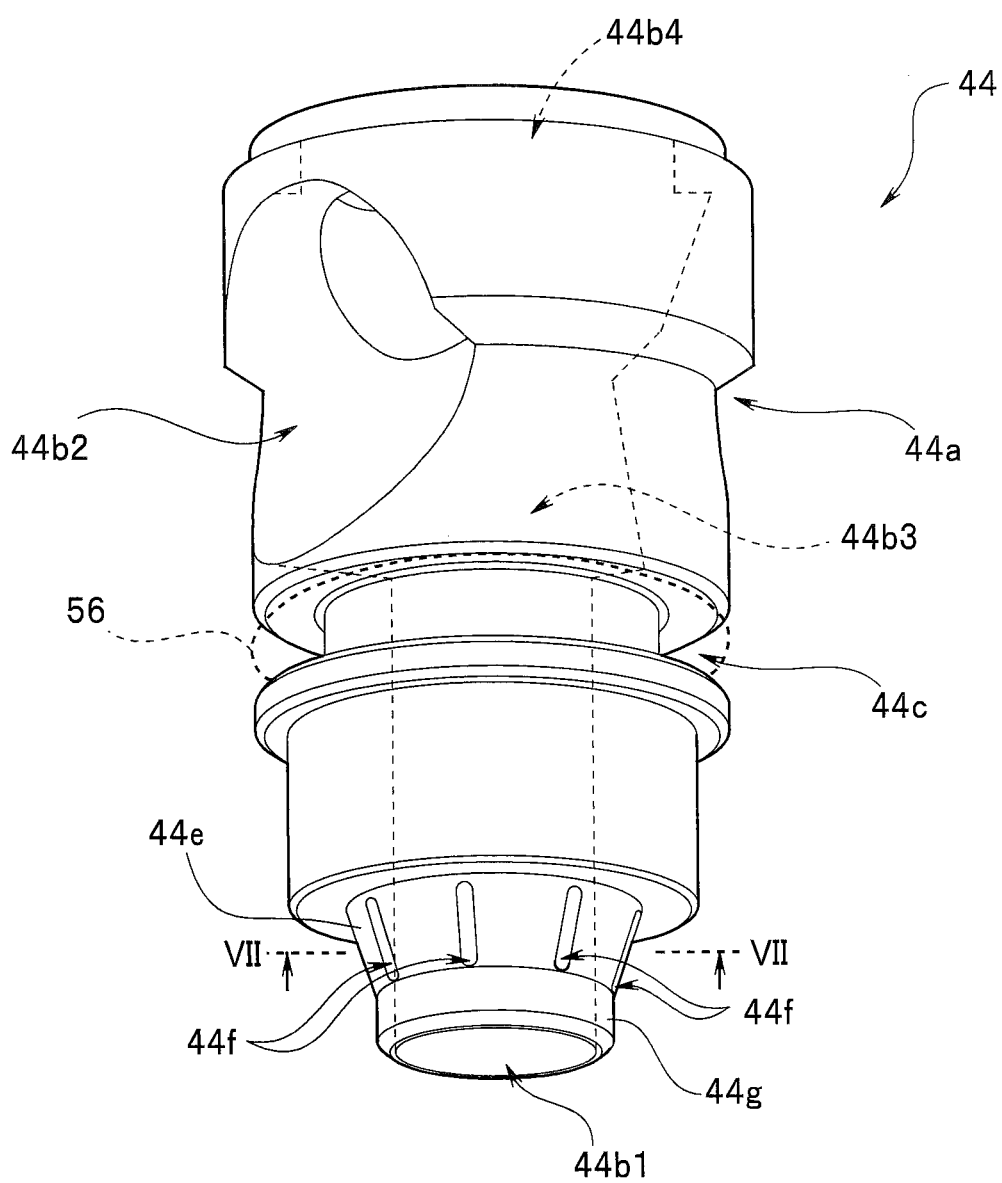
FIG. 5 is a perspective view of a fitting pressing member 44 according to the first embodiment of the present invention as viewed obliquely from underneath.

FIG. 5 is a perspective view of the fitting pressing member 44 as viewed obliquely from underneath. The fitting pressing member 44 has a cylindrical shape and includes the hollow portion 44b3 inside. A recess portion 44a is formed along the circumferential direction in an outer circumferential face of the fitting pressing member 44.

Furthermore, the first opening 44b1 is formed in a lower portion of the fitting pressing member 44. An opening 44b2 is formed in a side face of the fitting pressing member 44. The fitting pressing member 44 includes the hollow portion 44b3 inside, the hollow portion 44b3 bringing the first openings 44b1 and 44b into communication with each other. The opening 44b2 communicably connects the hollow portion 44b3 inside the cylindrical fitting pressing member 44 and the outside.

In other words, the first opening 44b1 is an opening that opens inside the endoscope fitting 11, and the opening 44b2 is an opening that is communicably connected to the first opening 44b1 and is connectable to a fluid supply source via the tube connection portion 42a.

In an outer circumferential face below the opening 44b2 of the fitting pressing member 44, a groove along the circumferential direction, that is, an outer circumferential groove 44c is formed. An O-shaped ring 56 is attached to the outer circumferential groove 44c.

In an opening 44b4 in an upper face of the fitting pressing member 44, an annular step portion 44d is formed. On the step portion 44d, a spring 54 is arranged. Upon the lid member 43 being secured to the upper portion of the body 42 via an adhesive, an upper part of the spring 54 enters the recess portion 43c of the extension portion 43b in the lid member 43 and a lower part of the spring 54 abuts the step portion 44d of the fitting pressing member 44, whereby the spring 54 is arranged in a compressed state between a bottom face 43c1 of the recess portion 43c and the step portion 44d.

Therefore, the fitting pressing member 44 is biased downward relative to the lid member 43 by means of an elastic force generated as a result of the spring 54 being urged to expand.

Furthermore, the fitting pressing member 44 includes a narrowing portion 44e at a lower portion. The narrowing portion 44e includes a part that tapers downward. In the present embodiment, the narrowing portion 44e has a conical shape. In other words, the narrowing portion 44e provides a narrowing portion that covers a part of the hollow portion 44b3 and has a side face whose outer diameter increases from a predetermined position of the fitting pressing member 44 (position PL of a boundary between a later-described cylindrical portion 44g and the narrowing portion 44e) toward the opening 44b2.

In a surface of the annular narrowing portion 44e, a plurality of grooves 44f formed along an axis direction are formed. The plurality of grooves 44f have shapes that are mutually the same, and the grooves have the same length, the same width and the same depth. The plurality of grooves 44f are each formed over a predetermined area from the predetermined position in the outer surface of the narrowing portion 44e.

As described above, the fitting pressing member 44, which is an endoscope connection instrument, is biased to the narrowing portion 44e side by the spring 54, which is an elastic member, inside the body 42, which is a body member.

Figure 6:
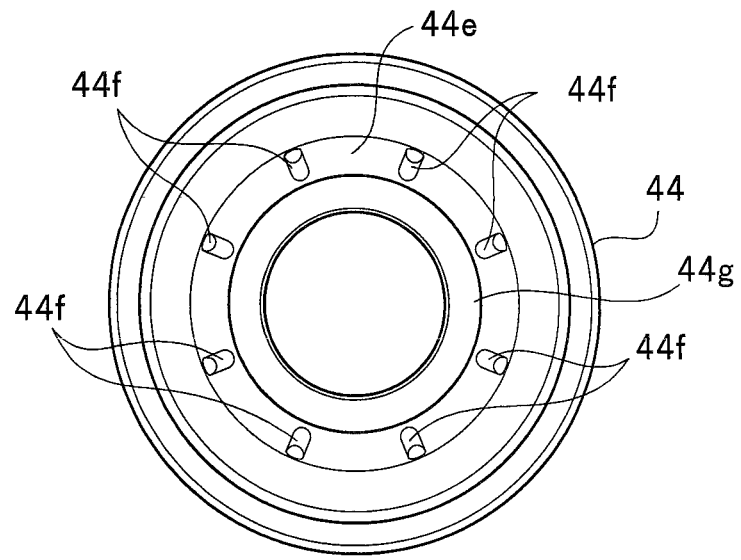
FIG. 6 is a bottom view of the fitting pressing member 44 according to the first embodiment of the present invention as viewed from underneath.
Figure 7:
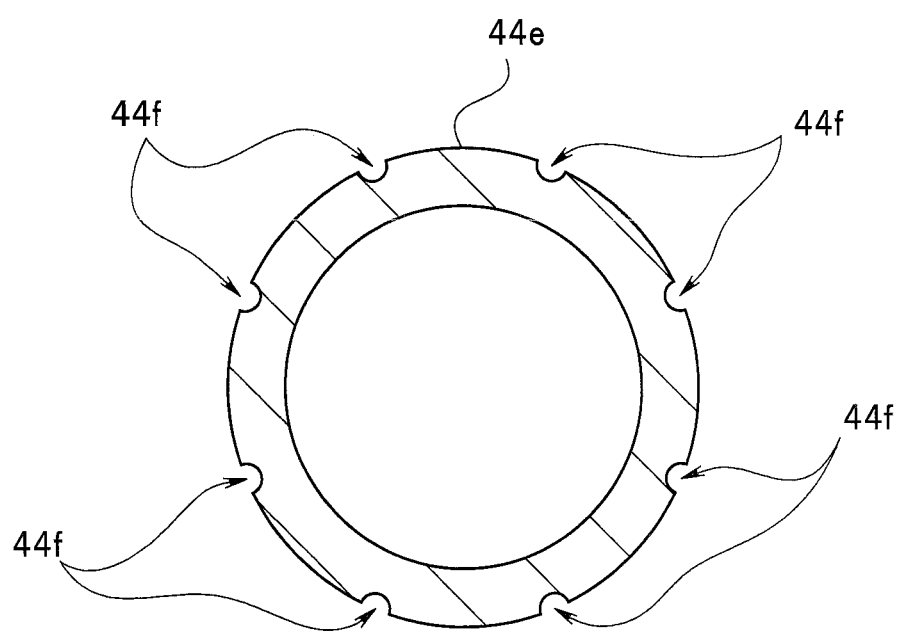
FIG. 7 is a cross-sectional view of a narrowing portion 44e along line VII-VII in FIG. 5.
Figure 8:
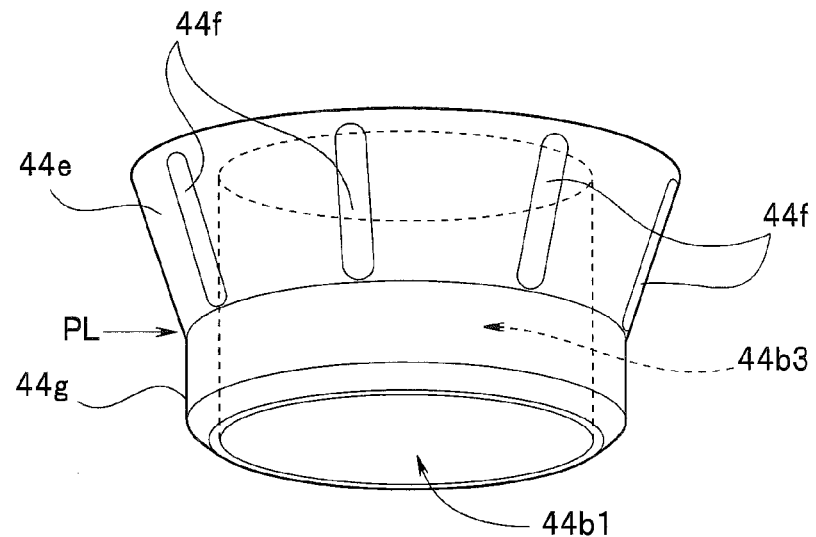
FIG. 8 is a perspective view of the part of the narrowing portion 44e and a cylindrical portion 44g according to the first embodiment of the present invention as viewed from obliquely underneath.

FIG. 6 is a bottom view of the fitting pressing member 44 as viewed from underneath. FIG. 7 is a cross-sectional view of the narrowing portion 44e along line VII-VII in FIG. 5. Here, eight grooves 44f are formed at regular intervals along a longitudinal axis direction of the fitting pressing member 44 in the surface of the narrowing portion 44e, and are symmetrical to one another with reference to a center axis. FIG. 8 is a perspective view of the part of the narrowing portion 44e and the cylindrical portion 44g as viewed obliquely from underneath.

As illustrated in FIGS. 6 to 8, the plurality of grooves 44f are arranged so as to be symmetrical to one another with reference to the center axis of the narrowing portion 44e, which is a narrowing portion. Each of the plurality of grooves 44f is formed so as to have a desired depth determined taking, e.g., a fluid leakage amount into account. It is desirable that the grooves 44f have a depth that is constant from a distal end to a rear end. Furthermore, each of the plurality of grooves 44f is formed along the axis direction of the narrowing portion 44e, which is a narrowing portion, although not parallel to the center axis of the fitting pressing member 44.

Note that here, the plurality of grooves 44f have the same length, but all of the lengths of the plurality of grooves 44f do not need to be the same.

Furthermore, the fitting pressing member 44 includes a cylindrical portion 44g that extends downward from the narrowing portion 44e.

The cylindrical portion 44g is provided so as to extend downward from an end portion of the narrowing portion 44e. In the fitting pressing member 44, the cylindrical portion 44g is provided from the lower opening to the predetermined position PL, and the inner hollow portion 44b3 exists inside the narrowing portion 44e and the cylindrical portion 44g. Therefore, the cylindrical portion 44g covers a part of the hollow portion 44b3 communicably connected to the first opening 44b1 and the opening 44b2 and is formed from the first opening 44b1 to the predetermined position PL.

As described above, the cylindrical fitting pressing member 44 includes the cylindrical portion 44g on the first opening 44b1 side to which the fitting 11 is attached, and the cylindrical portion 44g is formed from the first opening 44b1 to the predetermined position PL. Also, the fitting pressing member 44 includes the narrowing portion 44e whose outer diameter increases from an end portion of the cylindrical portion 44g in a direction opposite to the first opening 44b1. The cylindrical portion 44g and the narrowing portion 44e are formed so as to cover the inner hollow portion 44b3.

The narrowing portion 44e abuts and is pressed against an inside edge portion of the fitting 11 when the narrowing portion 44e is in line contact with the inside edge portion of the fitting 11.

(Operation)

An operation when the above-described connector 41 is attached to the fitting 11 of the endoscope 2 will be described.

Figure 9:
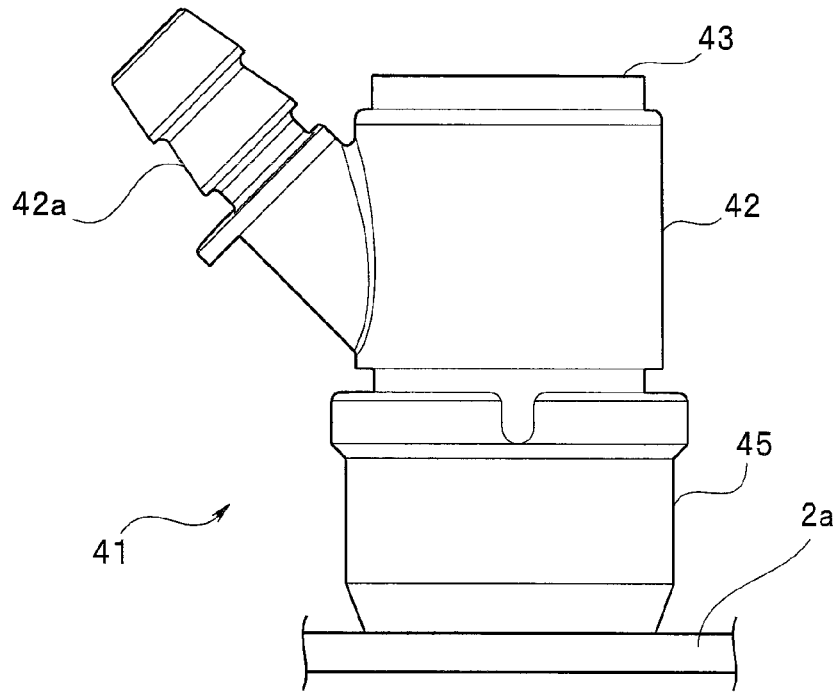
FIG. 9 is a front view illustrating a state in which the connector 41 is attached to a fitting 11 of an endoscope 2, according to the first embodiment of the present invention.
Figure 10:
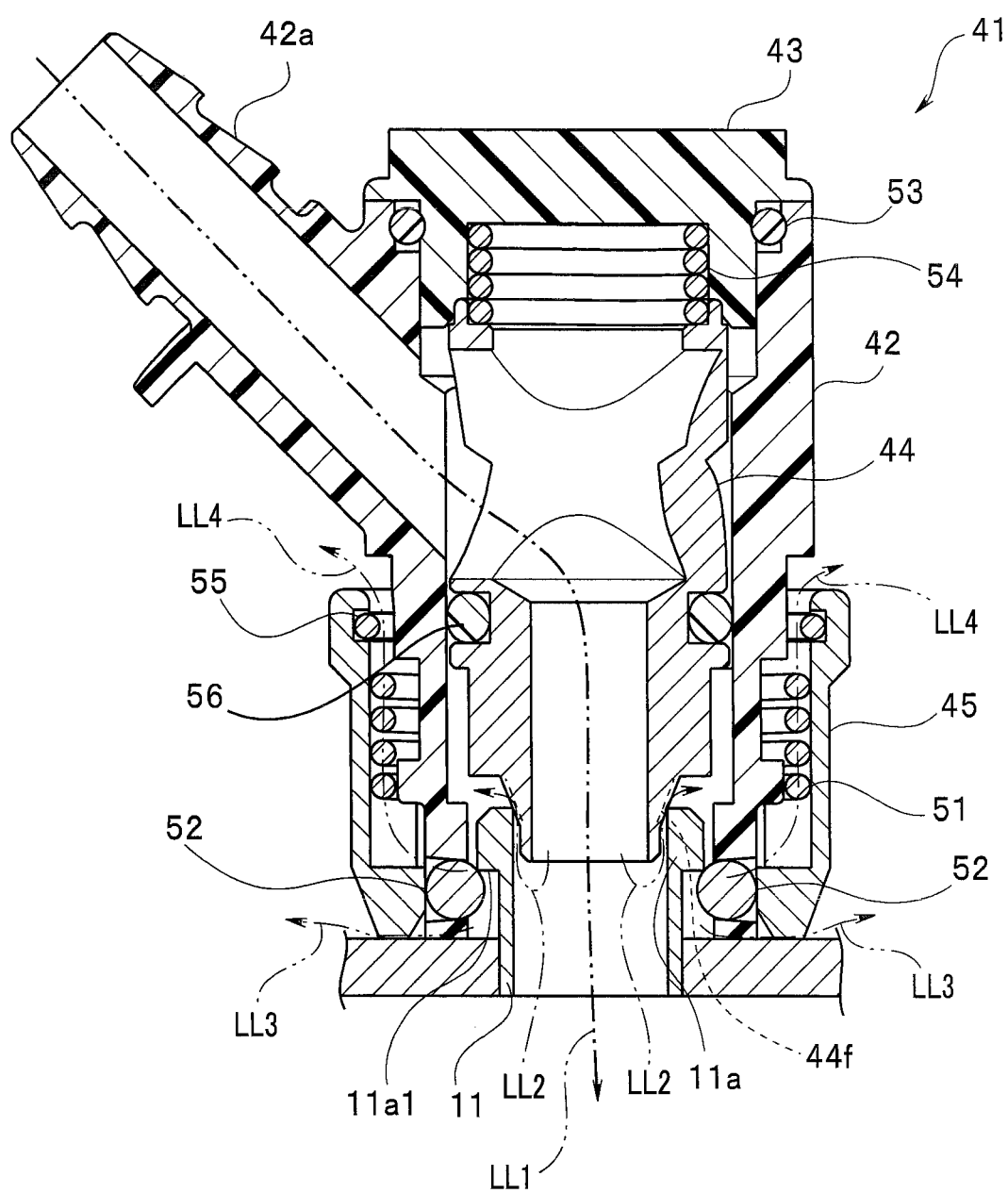
FIG. 10 is a cross-sectional view illustrating a state in which the connector 41 is attached to the fitting 11, according to the first embodiment of the present invention.

FIG. 9 is a front view illustrating a state in which the connector 41 is attached to the fitting 11 of the endoscope 2. FIG. 10 is a cross-sectional view illustrating a state in which the connector 41 is attached to the fitting 11.

When the connector 41 is attached to the fitting 11, the body 42 is pressed against the fitting 11 so that the narrowing portion 44e of the fitting pressing member 44 is fitted in and pressed into an opening of the fitting 11 of the endoscope 2.

As a result, the narrowing portion 44e is pushed upward inside the body 42, whereby the spring 54 is compressed. When the cover member 45 is pressed to the endoscope 2 side in the state in which the spring 54 is compressed, providing a state in which the four balls 52 can enter the lower face 11a1 side of an outward flange portion 11a of the fitting 11. Consequently, the inward flange portion 45b of the cover member 45 can press the respective balls 52 inward in a radial direction of the body 42.

Therefore, a part of each ball 52 protrudes from the inside of the corresponding hole 42e and butts an outer circumferential edge on the lower side of the outward flange portion 11a of the fitting 11, preventing the connector 41 from coming off from the fitting 11. Then, as illustrated in FIG. 9, a lower face of the cover member 45 abuts a surface of a sheath member 2a of the endoscope 2 in such a manner that the lower face is in close contact with and thereby secured to the surface.

In other words, the cover member 45 covering the body 42 has a securing mechanism that when the fitting pressing member 44, which is an endoscope connection instrument, is attached to the fitting 11 of the endoscope 2, secures the fitting pressing member 44 to the fitting 11.

As indicated by alternate long and two short dashes line LL1 in FIG. 10, a liquid such as a cleaning liquid is supplied from the cleaning tube 40 with the connector 41a connected to a port 37 for air/water feeding/forceps port in the endoscope cleaning/disinfecting apparatus 1 to a duct inside the endoscope 2 through the fitting 11. The liquid such as a cleaning liquid enters from the opening 44b2 communicably connected to the endoscope cleaning/disinfecting apparatus 1, which is a fluid supply source, passes through the inner hollow portion 44b3, and is discharged from the first opening 44b1 that opens inside the fitting 11 of the endoscope 2, into the duct inside the endoscope 2, for example, a treatment instrument insertion channel.

Also, as indicated by alternate long and two short dashes line LL2 in FIG. 10, the liquid discharged from the first opening 44b1 passes through the plurality of grooves 44f between the narrowing portion 44e and the inside edge portion of the fitting 11 that are in line contact with each other, and flows also to the inside of the body 42.

The liquid that that has flowed to the inside of the body 42 flows out from a gap between the cover member 45 and the sheath member 2a of the endoscope 2 as indicated by alternate long and two short dashes line LL3 in FIG. 10, and/or passes between the cover member 45 and the body 42 via the holes 42e provided in the body 42 and flows outside of the connector 41 as indicated by alternate long and two short dashes line LL4.

Here, since in the fitting 11 and the fitting pressing member 44, the surface of the narrowing portion 44e and the inside edge portion of the fitting 11 are in mere line contact with each other, the liquid such as a cleaning liquid comes into contact with almost an entire outer surface of the fitting 11, providing enhancement in capability of cleaning/disinfecting the fitting 11.

Furthermore, the connector 41 attached to the fitting 11 may rattle relative to the fitting 11 because of, e.g., a force imposed on the cleaning tube 40.

However, since the cylindrical portion 44g extends from the narrowing portion 44e, in the case of such rattling, the cylindrical portion 44g butts an inner circumferential face of the fitting 11, whereby inclination of the connector 41 is restricted.

Figure 11:
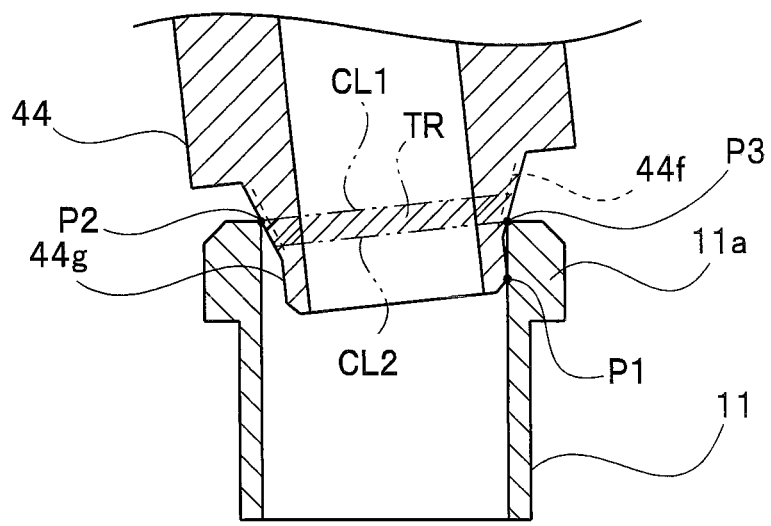
FIG. 11 is a diagram for describing a state in which the fitting pressing member 44 is most inclined because of the connector 41 rattling, according to the first embodiment of the present invention.

FIG. 11 is a diagram for describing a state in which the fitting pressing member 44 is inclined most as a result of the connector 41 rattling. As illustrated in FIG. 11, upon the fitting pressing member 44 being inclined and the cylindrical portion 44g thereby hitting against the inner circumferential face of the fitting 11 at point P1, the fitting pressing member 44 cannot be inclined any further. In other words, the cylindrical portion 44g provides an inclination restricting portion that restricts inclination of the fitting pressing member 44. Therefore, the cylindrical portion 44g restricts the fitting pressing member 44 from being inclined at an angle that is equal to or exceeds a predetermined angle, providing the effect of preventing a sharp decrease in outflow amount of a liquid from the first opening 44b1 when the fitting pressing member 44 is inclined and thus stabilizing the outflow amount.

Also, although as illustrated in, e.g., FIG. 8, the plurality of grooves 44f are provided over a large area of the narrowing portion 44e along the axis direction of the cylindrical portion 44g, in consideration of the aforementioned rattling of the connector 41, each groove 44f only needs to be formed so as to include at least an area TR that comes into contact with the inside edge portion of the fitting 11, which is illustrated in FIG. 11, in a maximum range of rattling. In other words, a structure in which the respective grooves 44f all have a dent in the area TR and the dents of some of the grooves 44f further extend downward or upward may be provided. In FIG. 11, the fitting pressing member 44 is inclined, a position at point P2 on the upper side of the narrowing portion 44e is in contact with the inside edge portion of the fitting 11, and a position at point P3 on the lower side of the narrowing portion 44e is in contact with the inside edge portion of the fitting 11. Therefore, the area TR is a region extending between a circumferential line CL1 that passes through point P2 in the narrowing portion 44e and a circumferential line CL2 that passes through point P3 in the narrowing portion 44e at the time of maximum rattling.

Also, since in the aforementioned TR, the plurality of grooves 44f are definitely located between the narrowing portion 44e and the inside edge portion of the fitting 11, even if the connector 41 is inclined relative to the fitting 11 because of rattling, a plurality of gaps between the plurality of grooves 44f and the fitting 11 do not largely change in size. Therefore, there is almost no change in amount of leakage of a liquid such as cleaning liquid from the plurality of gaps during cleaning and disinfecting.

In other words, each groove 44f only needs to be formed in the region of the contemplated area TR extending over a circumference of the narrowing portion 44e, which is indicated by the alternate long and two short dashes lines in FIG. 11.

Figure 12:
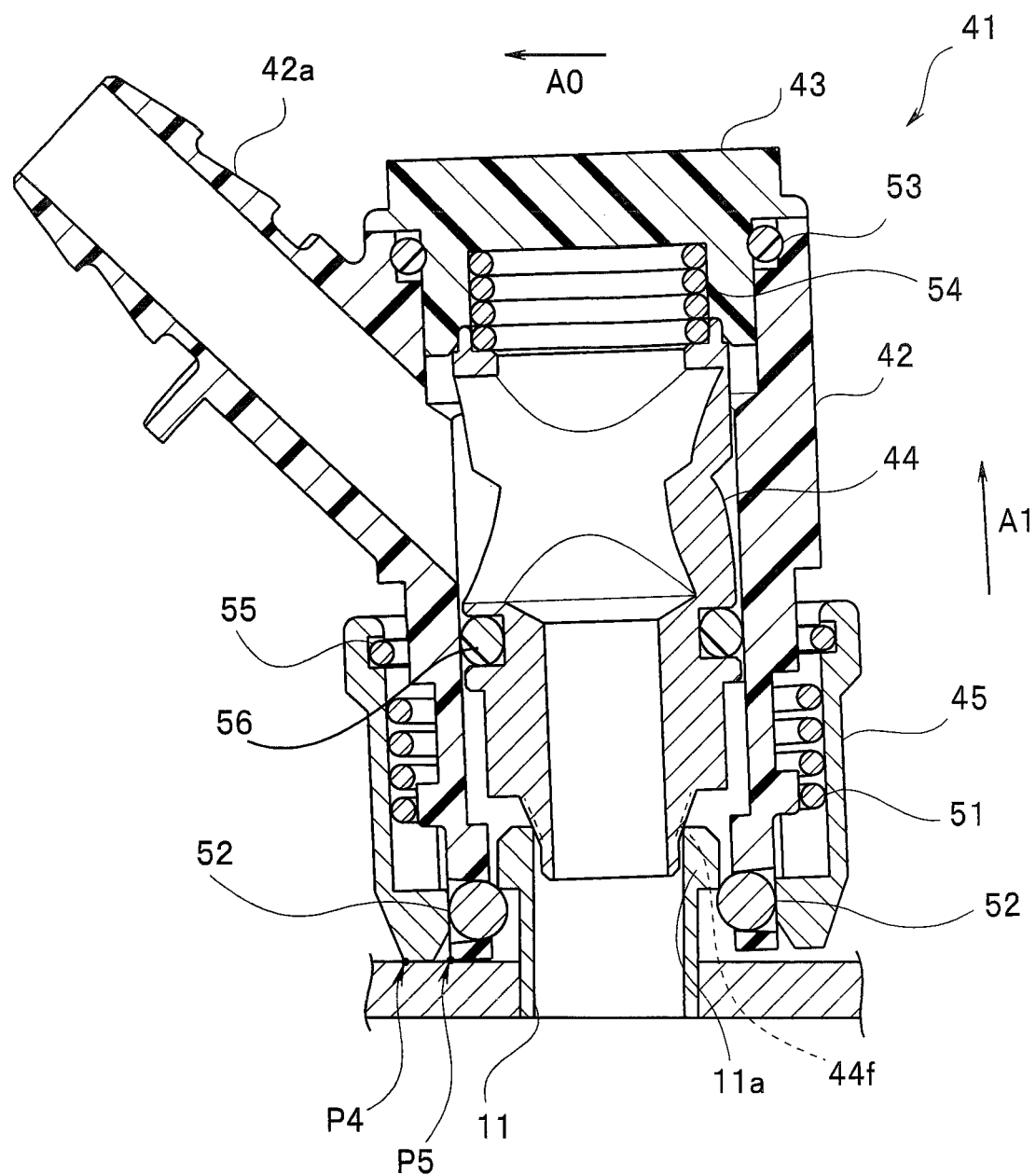
FIG. 12 is a diagram for describing a state in which the connector rattles, according to the first embodiment of the present invention.

Also, inclination of the connector 41 due to rattling such as described above is restricted also by the cover member 45 and the body 42. FIG. 12 is a diagram for describing a state when the connector rattles.

In FIG. 12, if the connector 41 is inclined as a result of a load being imposed thereon in a direction indicated by arrow A0, inclination of the fitting pressing member 44 is restricted by the cylindrical portion 44g of the fitting pressing member 44; however, for example, in FIG. 12, the connector 41 is inclined so as to lift in a direction indicated by arrow A1, a bottom portion of the cover member 45 butts the sheath member 2a of the endoscope 2 at point P4, whereby inclination of the connector 41 is restricted also by the cover member 45. Furthermore, likewise, a bottom portion of the body 42 butts the sheath member 2a of the endoscope 2 at point P5, whereby inclination of the connector 41 is restricted also by the body 42.

Therefore, with the connector 41 according to the present embodiment, inclination of the connector 41 is restricted not only by the cylindrical portion 44g of the fitting pressing member 44 butting the inner circumferential face of the fitting 11, but also by of the body 42 and the cover member 45 of the connector 41.

Note that although in the above-described example, the end portion of the cylindrical portion 44g hits against the inner circumferential face of the fitting 11, a rib, that is, an annular projection portion may be provided at the distal end portion of the cylindrical portion.

Figure 13:
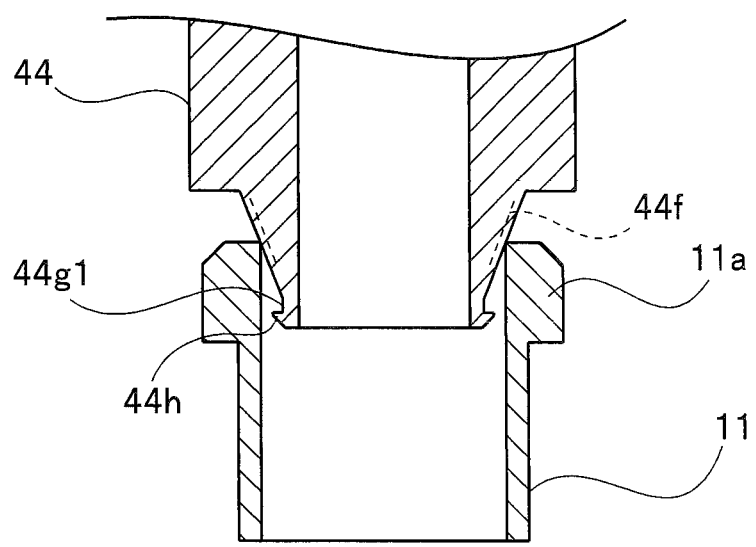
FIG. 13 is a diagram for describing an example in which a projection portion is provided at a distal end portion of a cylindrical portion of the fitting pressing member 44, according to the first embodiment of the present invention.

FIG. 13 is a diagram for describing an example in which a projection portion is provided at the distal end portion of the cylindrical portion of the fitting pressing member 44. As illustrated in FIG. 13, an annular projection portion 44h is provided at a distal end portion of a cylindrical portion 44g1.

Therefore, inclination of the fitting pressing member 44 such as mentioned above can be restricted also by the projection portion 44h provided at the distal end portion of the cylindrical portion 44g1 illustrated in FIG. 13.

Still furthermore, although in the above-described example, as illustrated in FIG. 8, the narrowing portion has a shape that is a part of a conical shape, but may have a shape that is a part of a hemispherical shape.

Figure 14:
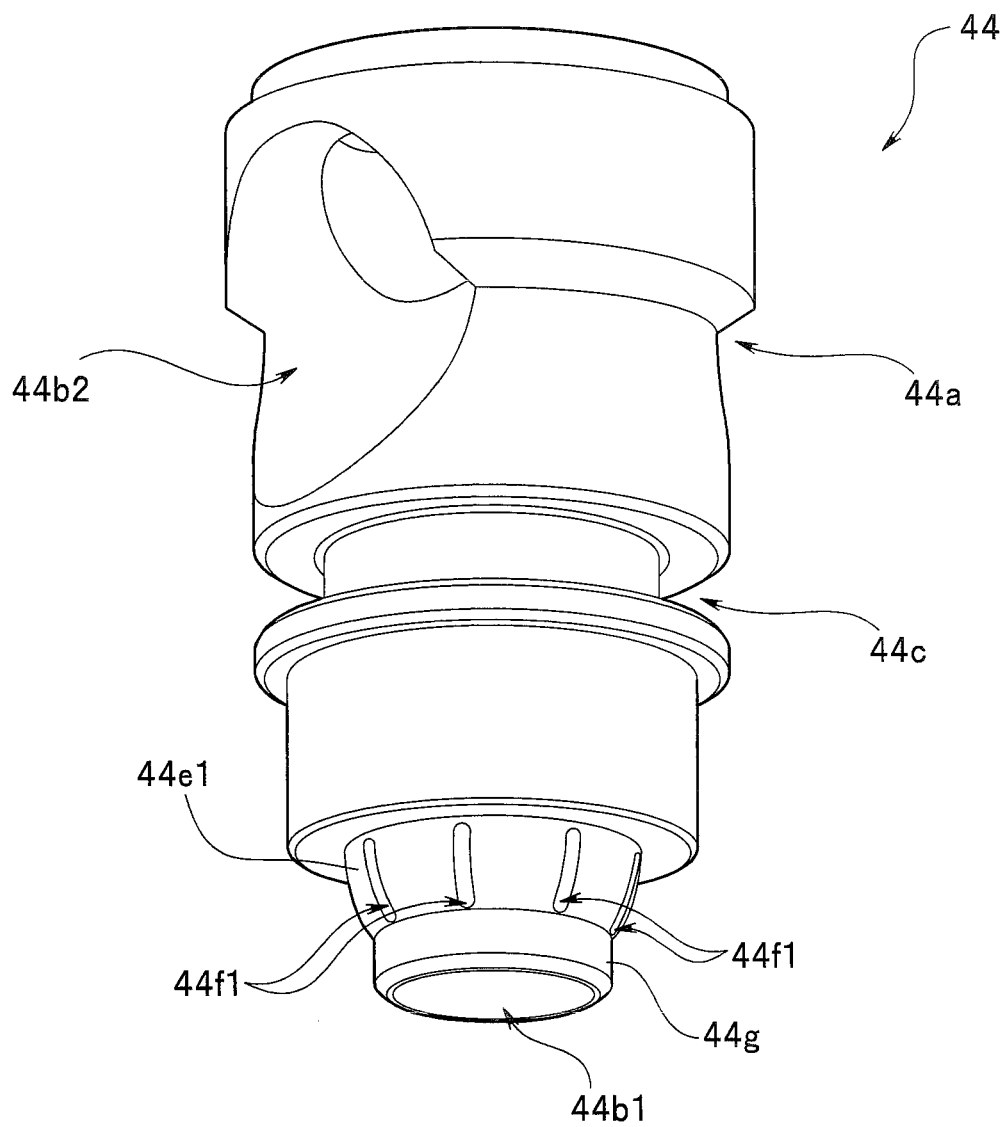
FIG. 14 is a perspective view of a fitting pressing member including a narrowing portion having a spherical zone shape as viewed obliquely from underneath, according to the first embodiment of the present invention.

FIG. 14 is a perspective view of a fitting pressing member including a narrowing portion having a spherical zone shape as viewed obliquely from underneath.

Although in the above-described example, the surface of the narrowing portion 44e, which is a narrowing portion, has a tapered shape, and is a partial face of a surface shape of a conical shape, the narrowing portion in FIG. 14 has a bowl shape, and a surface thereof is a surface of a spherical zone shape.

A narrowing portion 44e1 of a fitting pressing member 44 in FIG. 14 has a surface shape obtained by cutting a hemisphere along two planes. In other words, the narrowing portion 44e1 has a shape that is a part of a bowl. Therefore, the narrowing portion 44e1 of the fitting pressing member 44 in FIG. 14 consistently remains in line contact with the inner circumferential edge portion of the fitting 11, which has a circular shape, even upon occurrence of rattling, which is described with reference to FIG. 11.

Accordingly, an amount of leakage of a liquid such as a cleaning liquid from the plurality of gaps during cleaning and disinfecting is consistently the same.

As described above, the present embodiment enables provision of an endoscope connection instrument that can reliably clean and disinfect a fitting part communicably connected to a duct inside an endoscope.

Also, because of the simplicity of the configuration of the endoscope connection instrument according to the present embodiment, the present embodiment enables provision of an endoscope connection instrument that can reliably clean and disinfect a fitting part communicably connected to a duct inside an endoscope with a simple configuration.

Note that the above-described connector 41 can also be regarded as an endoscope connection instrument.

Second Embodiment

Although the connector 41 according to the first embodiment includes the fitting pressing member 44, the body 42 including the tube connection portion 42a to which the cleaning tube 40 is to be connected, and the cover member 45, a connector according to a second embodiment includes a fitting pressing member and a securing member.

Components and configuration parts of the connector according to the present embodiment that are the same as those of the first embodiment are provided with reference numerals that are the same as those of the first embodiment, and description thereof will be omitted.

Figure 15:
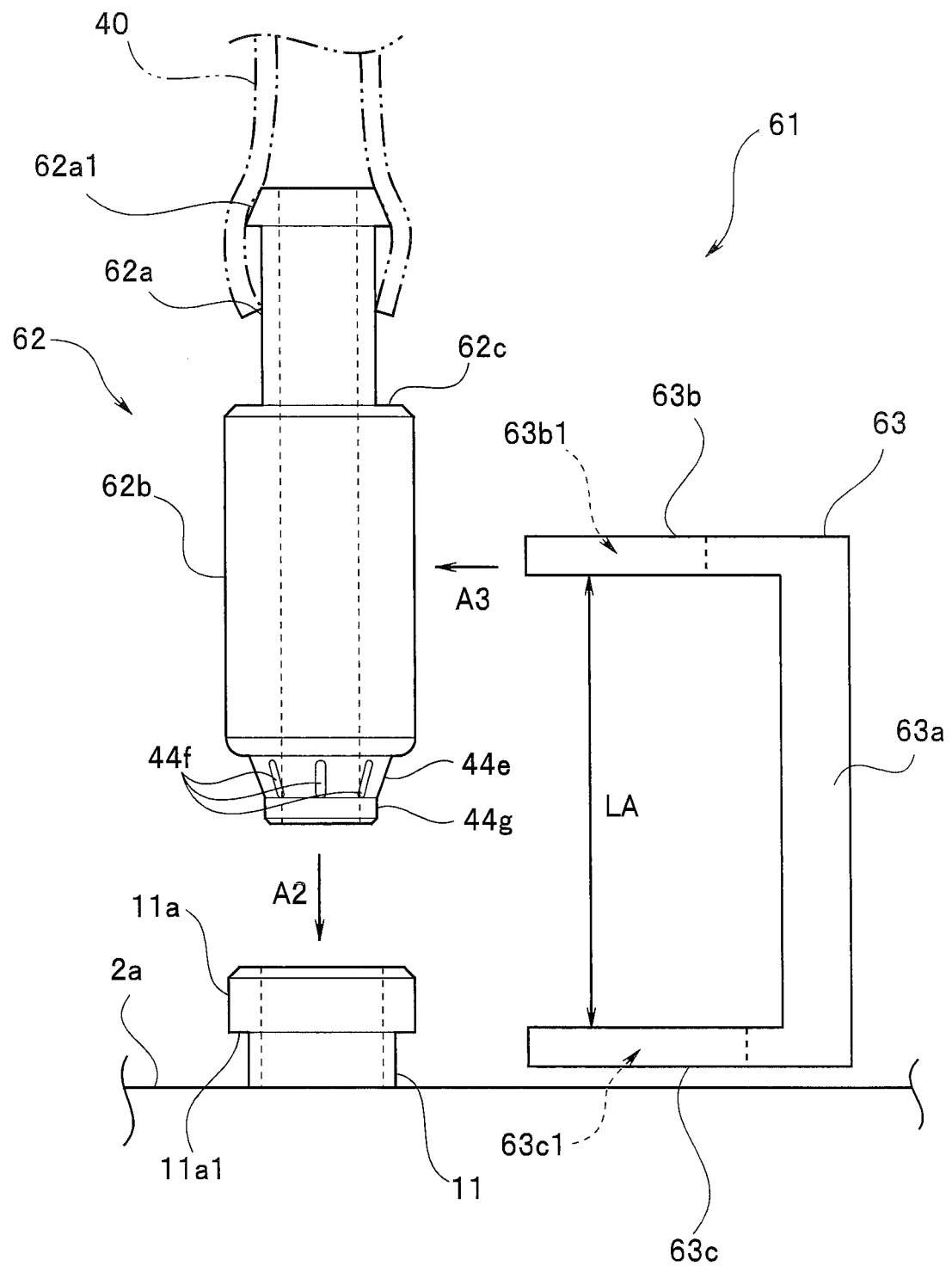
FIG. 15 is a diagram for describing a state before a connector according to a second embodiment of the present invention is attached to a fitting.

FIG. 15 is a diagram for describing a state before a connector according to the present embodiment is attached to a fitting.

As illustrated in FIG. 15, a connector 61 according to the present embodiment includes a fitting pressing member 62, which is an endoscope connection instrument, and a securing member 63. The connector 61 is a connector provided at one end of a cleaning tube 40 to be connected to an endoscope cleaning/disinfecting apparatus 1, and at the other end of the cleaning tube 40, a connector 41a is provided, and the connector 41a is to be connected to a port 37 for an air/water feeding/forceps port in the endoscope cleaning/disinfecting apparatus 1.

The fitting pressing member 62 is made of a metal such as a stainless steel and has a cylindrical shape. At a proximal end portion of the fitting pressing member 62, a tube connection portion 62a for connecting the cleaning tube 40 to the fitting pressing member 62 is provided. The tube connection portion 62a includes a circumferential projection portion 62a1 for increasing a diameter of the cleaning tube 40 from the inside and thereby securing the cleaning tube 40, which is made of a resin, to an outer circumferential portion.

At a distal end portion of the fitting pressing member 62, a narrowing portion 44e and a cylindrical portion 44g are provided toward a distal end. A plurality of grooves 44f are formed in an outer circumferential face of the narrowing portion 44e.

Note that although, here, the narrowing portion 44e has a shape that is a part of a conical shape, the narrowing portion 44e may have a spherical zone shape such as illustrated in FIG. 14.

The fitting pressing member 62 includes a diameter-increased portion 62b between the tube connection portion 62a and the narrowing portion 44e. The diameter-increased portion 62b includes a step portion 62c at a boundary portion between the tube connection portion 62a and the diameter-increased portion 62b on the proximal end side.

The securing member 63 is a resin plate member and has a squared U shape. In respective arm portions 63b and 63c at opposite ends of a shaft portion 63a of the securing member 63, cutout portions 63b1 and 63c1 that receive the fitting pressing member 62 and a fitting 11, respectively, are formed (see FIG. 16).

As illustrated in FIG. 15, a distance LA between the arm portions 63b and 63c on the opposite sides of the securing member 63 is substantially the same or shorter than a distance between a lower face 11a1 of an outward flange portion of the fitting 11 and the step portion 62c of the diameter-increased portion 62b in a state in which the narrowing portion 44e of the fitting pressing member 62 is inserted in an opening of the fitting 11.

The narrowing portion 44e of the fitting pressing member 62 is inserted to the inside of the fitting 11 along a direction indicated by arrow A2, and subsequently, the securing member 63 is attached along a direction indicated by arrow A3 so that the cutout portions 63b1 and 63c1 receive the fitting pressing member 62 and the fitting 11, respectively, whereby the fitting pressing member 62 is secured to the fitting 11 by the securing member 63.

In other words, the securing member 63 is a securing member that secures the fitting pressing member 62 to the fitting 11 in a state in which a distal end of the narrowing portion 44e is inserted in the fitting 11.

Figure 16:
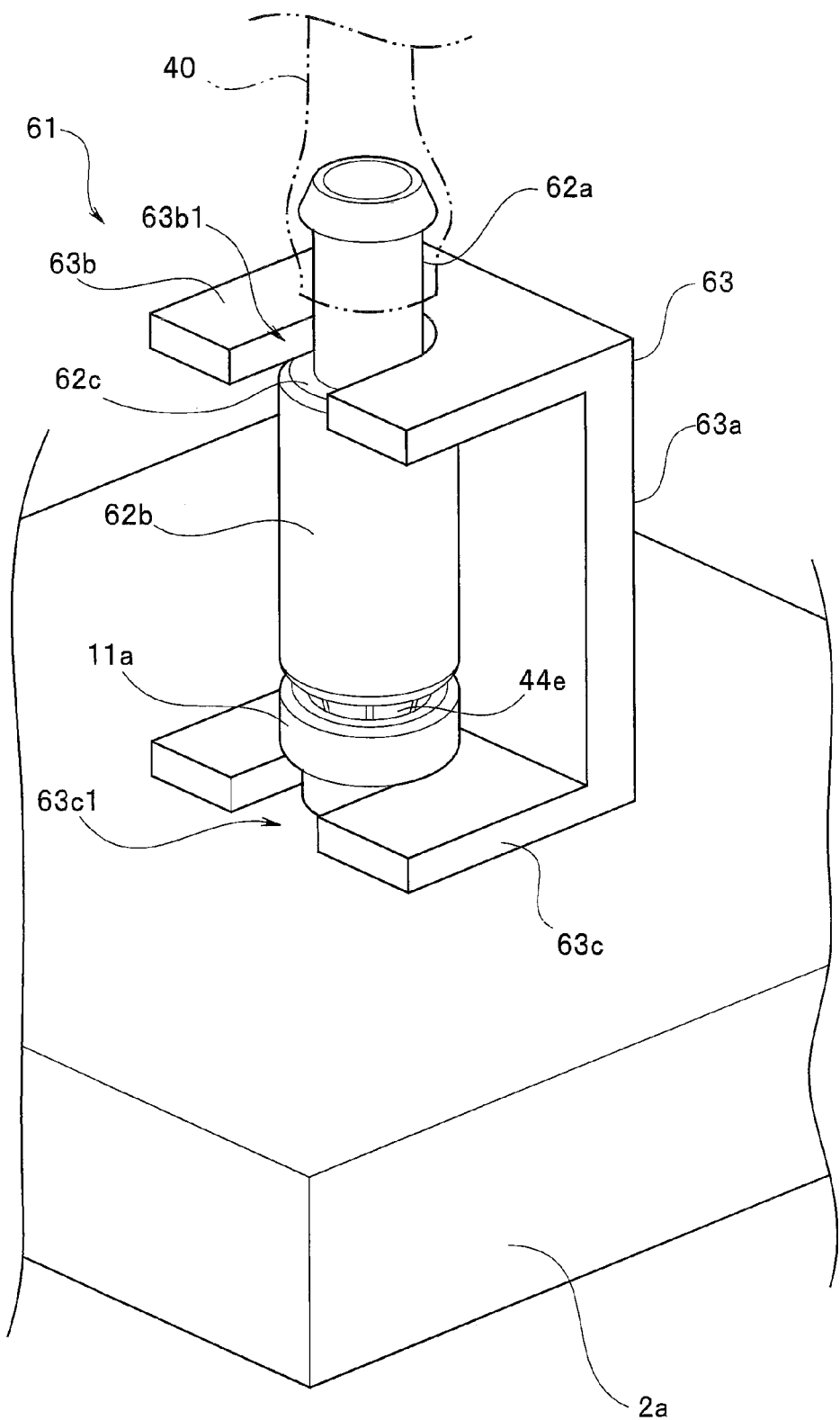
FIG. 16 is a perspective view illustrating a state in which a fitting pressing member 62 is fixed to a fitting 11 via a securing member 63, according to the second embodiment of the present invention.
Figure 17:
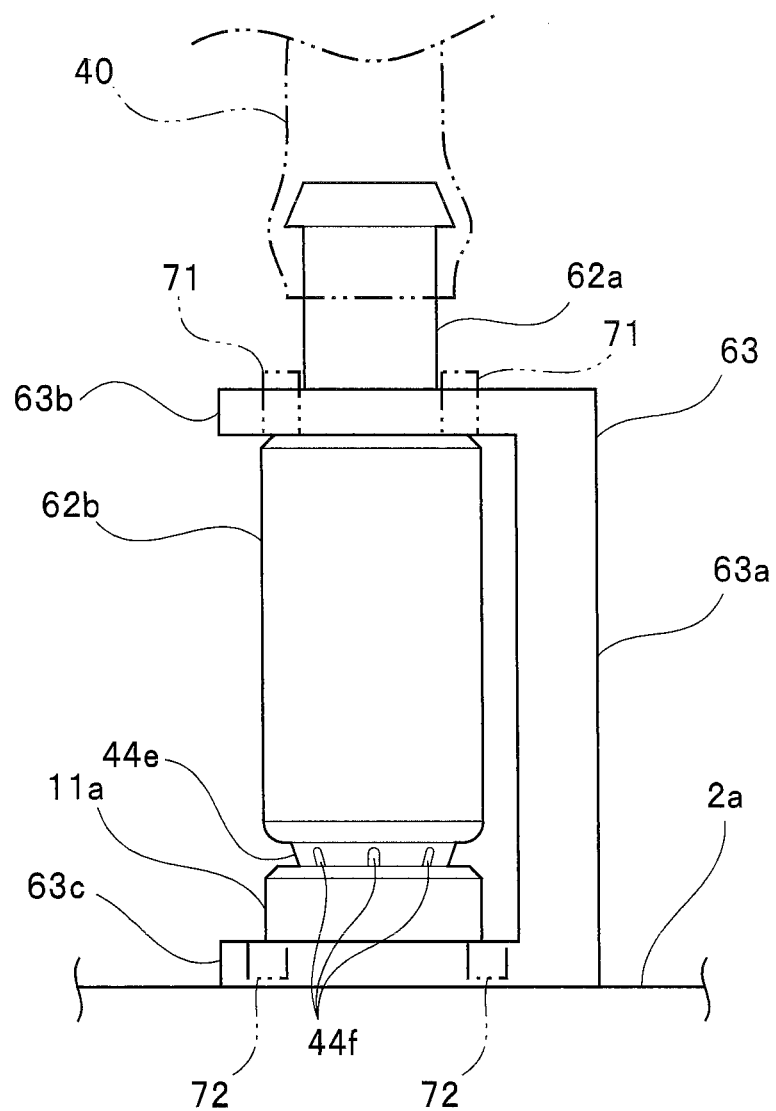
FIG. 17 is a front view illustrating a state in which the fitting pressing member 62 is secured to the fitting 11 via the securing member 63, according to the second embodiment of the present invention.

FIG. 16 is a perspective view illustrating a state in which the fitting pressing member 62 is secured to the fitting 11 by the securing member 63. FIG. 17 is a front view illustrating a state in which the fitting pressing member 62 is secured to the fitting 11 by the securing member 63.

As illustrated in FIGS. 16 and 17, in a state in which the narrowing portion 44e is inserted into the opening portion of the fitting 11, the fitting pressing member 62 is secured to the fitting 11 by the securing member 63. In this state, a liquid such as a cleaning liquid is supplied from the cleaning tube 40 into a duct communicably connected to the opening portion of the fitting 11, and the narrowing portion 44e is in line contact with an inside edge portion of the opening portion of the fitting 11. Therefore, the liquid such as a cleaning liquid comes into contact with almost an entire outer surface of the fitting 11, and thus, the entire fitting 11 is sufficiently cleaned and disinfected.

Note that although in the above-described example, the securing member 63 is a component that is separate from the endoscope 2 and the endoscope cleaning/disinfecting apparatus 1, the securing member may be a member secured to the endoscope cleaning/disinfecting apparatus 1. In other words, the securing member may be provided in the endoscope cleaning/disinfecting apparatus 1.

For example, in FIG. 17, a plurality of (here, four) projection members 71 and 72 such as indicated by the dotted lines are provided on a cleaning/disinfecting bath 23 so that the fitting pressing member 62 and the fitting 11 engage with the plurality of projection members 71 and 72, whereby the fitting pressing member 62 is secured to the fitting 11. The two projection members 71 come into contact with the step portion 62c of the diameter-increased portion 62b, and the two projection members 72 come into contact with the lower face 11a1 of the outward flange portion of the fitting 11. Then, a distance between the two projection members 71 and the two projection members 72 is substantially the same as the distance between the step portion 62c and the lower face 11a1 in a state in which the narrowing portion 44e is inserted in the opening portion of the fitting 11, or is slightly shorter than the distance between the step portion 62c and the lower face 11a1 in a state in which the narrowing portion 44e is inserted in the opening portion of the fitting 11.

Accordingly, the present embodiment enables provision of an endoscope connection instrument that can reliably clean and disinfect a fitting part communicably connected to a duct inside an endoscope.

Also, because of the simplicity of the configuration of the endoscope connection instrument according to the present embodiment, the present embodiment enables provision of an endoscope connection instrument that can reliably clean and disinfect a fitting part communicably connected to a duct inside an endoscope with a simple configuration.

Note that the above-described connector 61 can also be regarded as an endoscope connection instrument.

(Cleaning of Gas Button at Operation Portion)

When an operation portion 3 of an endoscope 2 is cleaned, the endoscope 2 is received in the cleaning/disinfecting bath 23 with a gas button provided at the operation portion 3 in a depressed state.

Figure 18:
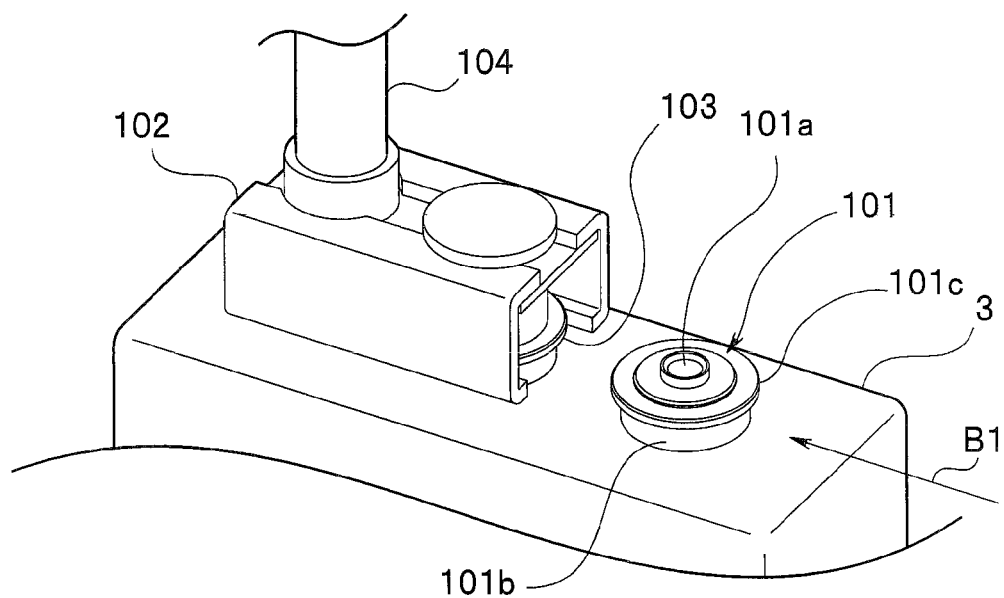
FIG. 18 is a diagram illustrating a state in which a sliding apparatus that receives supply of a liquid such as a cleaning liquid and supplies the liquid to an internal cylinder is attached in the vicinity of a gas button at an operation portion 3, according to an embodiment of the present invention.

FIG. 18 is a diagram illustrating a state in which a sliding apparatus that receives supply of a liquid such as a cleaning liquid and supplies the liquid to an internal cylinder is attached in the vicinity of a gas button at the operation portion 3.

At a surface of the operation portion 3 of the endoscope 2, various types of knobs and various types of buttons are provided, and one of such buttons is a gas button 101. The gas button 101 is a button to be operated when a predetermined gas is protruded from a distal end portion of an insertion portion 4, and upon the gas button 101 being depressed, an internal valve is opened and the predetermined gas is discharged from the distal end portion of the insertion portion 4 via a gas duct.

In the vicinity of the gas button, a suction cylinder and an air/water feeding cylinder are disposed, the sliding apparatus 102 engages with respective flange portions of these cylinders and is slid, and thereby attached to the suction cylinder and the air/water feeding cylinder. In FIG. 18, a part of the air/water feeding cylinder 103 is illustrated. At a tip portion of the gas button 101, a button operation member 101a protrudes from an opening portion of a support member 101b that supports the button operation member 101a so that the button operation member 101a can be depressed. The support member 101b includes an outward flange portion 101c at an upper portion.

A liquid supply tube 104 is connected to the sliding apparatus 102, and the sliding apparatus 102 is configured so as to, upon the sliding apparatus 102 being attached to the suction cylinder and the air/water feeding cylinder, supply a liquid such as a cleaning liquid from the tube 104 to the respective cylinders. During cleaning/disinfection, the liquid supplied from the tube 104 via the sliding apparatus 102 cleans/disinfects the inside of the two cylinders communicably interconnected inside, and the gas button 101 is depressed to provide a state in which the internal valve is opened, whereby the liquid such as a cleaning liquid is supplied into the gas duct, enabling the gas duct to be cleaned/disinfected. Here, an adapter 111 is attached to the gas button 101, enabling the gas button 101 to be brought into a depressed state.

Figure 19:
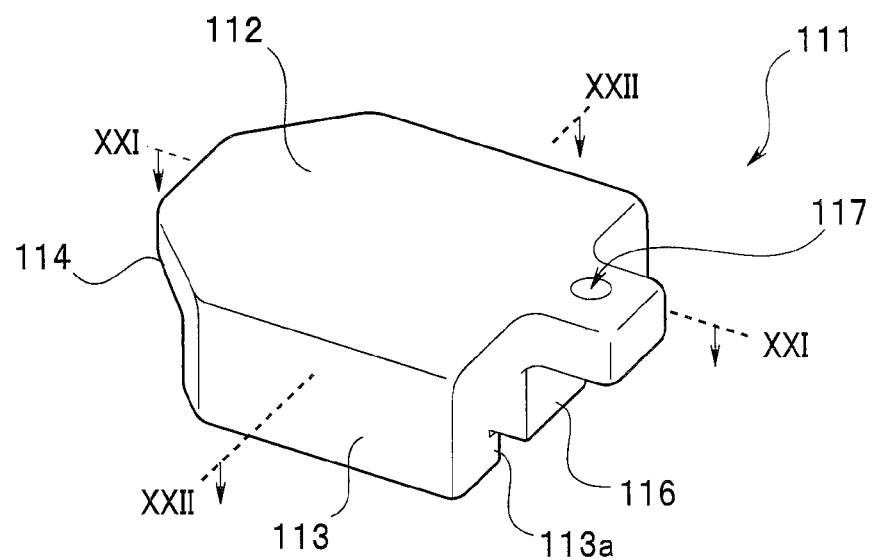
FIG. 19 is a perspective view of an adapter 111 for bringing a gas button 101 into a depressed state as viewed obliquely from above, according to the embodiment of the present invention.
Figure 20:
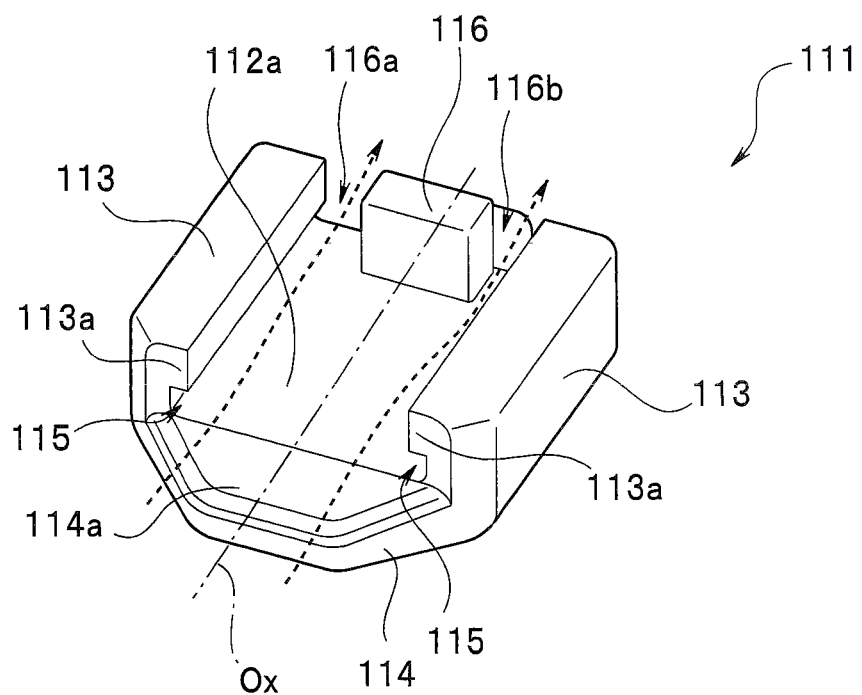
FIG. 20 is a perspective view of the adapter 111 as viewed obliquely from underneath, according to the embodiment of the present invention.
Figure 21:
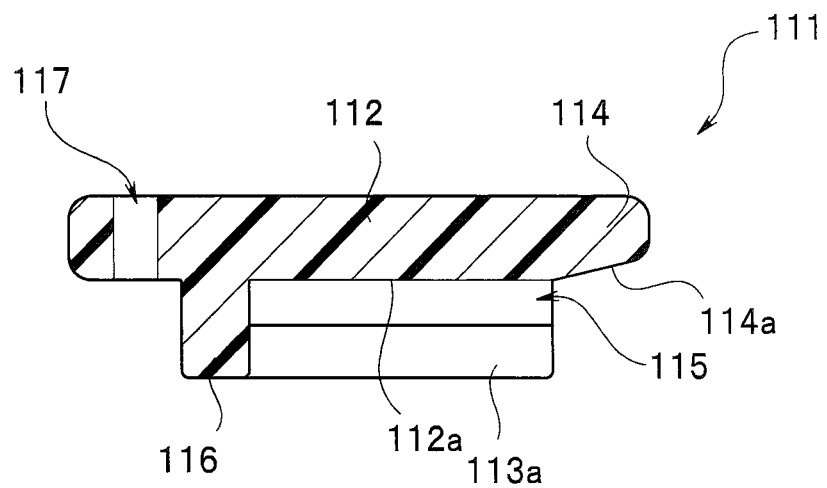
FIG. 21 is a cross-sectional view of the adapter 111 along line XXI-XXI in FIG. 19.
Figure 22:
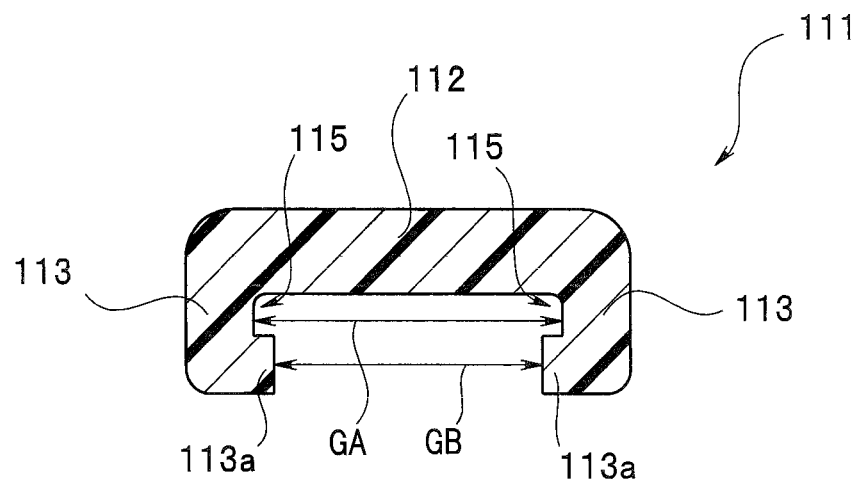
FIG. 22 is a cross-sectional view of the adapter 111 along line XXII-XXII in FIG. 19.

FIG. 19 is a perspective view of the adapter 111 for bringing the gas button 101 into a depressed state as viewed obliquely from above. FIG. 20 is a perspective view of the adapter 111 as viewed obliquely from underneath. FIG. 21 is a cross-sectional view of the adapter 111 along line XXI-XXI in FIG. 19. FIG. 22 is a cross-sectional view of the adapter 111 along line XXII-XXII in FIG. 19.

As illustrated in FIGS. 20 and 22, where a direction in which the adapter 111 is attached to the gas button 101 is an axis direction Ox, the adapter 111 has a squared U shape in a cross-section perpendicular to the axis direction Ox. The adapter 111 is made of a resin, and is a cap member including a plate-shaped portion 112, and side wall portions 113 on the opposite sides of the plate-shaped portion 112. Also, as illustrated in FIG. 22, end portions of the two side wall portions 113 include respective protrusion portions 113a that protrude in respective directions in which the protrusion portions 113a face each other. Furthermore, a groove 115 along the axis direction Ox is formed on the inner side of each side wall portion 113.

As described above, the gas button 101 has the outward flange portion 101c. The outward flange portion 101c has a size and a shape that allow the outward flange portion 101c to be inserted in the grooves 115. The outward flange portion 101c has an outer diameter that is smaller than a distance GA between respective bottom parts of the two grooves 115 facing each other, but is larger than a distance GB between the protrusion portions 113a facing each other. In other words, the adapter 111 is configured so that the distance GA between the respective bottom portions of the two grooves 115 facing each other is longer than the outward flange portion 101c and the distance GB between the two protrusion portions 113a facing each other is shorter than the outward flange portion 101c.

On the distal end side of the plate-shaped portion 112, a trapezoidal extension portion 114 is provided. On the proximal end side of the plate-shaped portion 112, a butting portion 116 that the gas button 101 butts, the butting portion 116 protruding in a direction that is the same as the direction in which the side wall portions 113 protrude is provided.

Between the side wall portions 113 on the opposite sides of the butting portion 116, gaps 116a and 116b are formed, whereby, as described later, a liquid such as a cleaning liquid that has flowed in from the extension portion 114 side easily flows through the gaps 116a and 116b.

The plate-shaped portion 112 includes a flat surface 112a on the inner side of the adapter 111 having a squared U shape. Furthermore, the extension portion 114 on the distal end side of the plate-shaped portion 112 includes an inclined surface 114a. As illustrated in FIG. 21, the inclined surface 114a is a surface that is continuous with the flat surface 112a, and the inclined surface 114a is formed in such a manner that a thickness of the extension portion 114 gradually decreases from the flat surface 112a toward a distal end portion of the extension portion 114.

Also, the adapter 111 includes a hole 117 for putting a piece of string for loss prevention, on the side opposite to the extension portion 114.

An operation of the adapter 111 having the above-described configuration will be described.

The adapter 111 is attached to the gas button 101 in a direction illustrated in arrow B1 in FIG. 18 so that the flange portion 101c of the gas button 101 is inserted in the groove 115.

Figure 23:
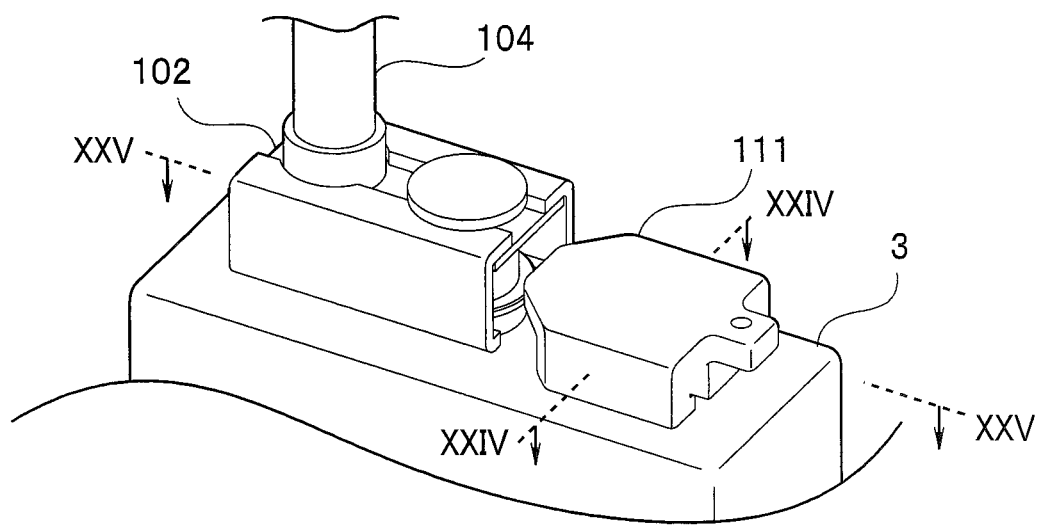
FIG. 23 is a perspective view illustrating a state in which the adapter 111 is attached to the gas button 101, according to the embodiment of the present invention.
Figure 24:
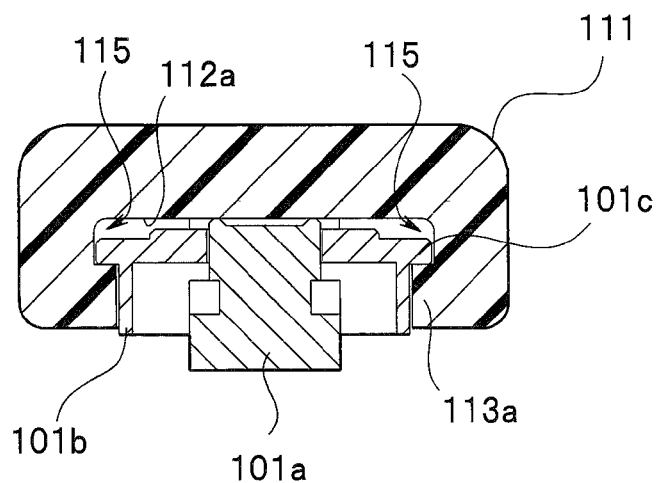
FIG. 24 is a cross-sectional view of the adapter 111 along line XXIV-XXIV in FIG. 23 and illustrates a state in which the adapter 111 is attached to the gas button 101.
Figure 25:
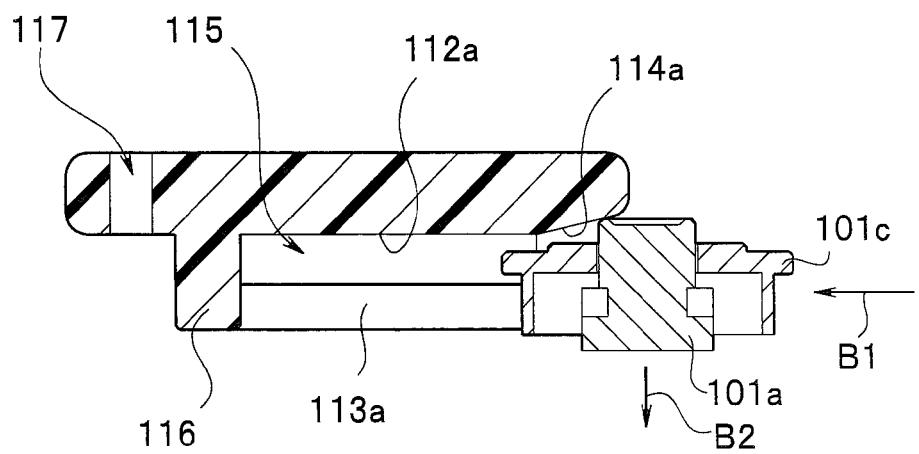
FIG. 25 is a cross-sectional view of the adapter 111 along line XXV-XXV in FIG. 23 and illustrates a state of the adapter 111 at a certain position in the course of the adapter 111 being attached to the gas button 101.

FIG. 23 is a perspective view illustrating a state in which the adapter 111 is attached to the gas button 101. FIG. 24 is a cross-sectional view of the adapter 111 along line XXIV-XXIV in FIG. 23 and illustrates a state in which the adapter 111 is attached to the gas button 101. FIG. 25 is a cross-sectional view of the adapter 111 along line XXV-XXV in FIG. 23 and illustrates a state at a certain point during the adapter 111 being attached to the gas button 101.

When the adapter 111 is attached to the gas button 101, the adapter 111 is attached to the gas button 101 in the direction indicated by arrow B1 so that the outward flange portion 101c is inserted in the groove 115.

As illustrated in FIG. 25, the outward flange portion 101c is restricted from moving upward/downward in the groove 115, and thus, even if the adapter 111 moves toward the gas button 101, the support member 101b does not move upward/downward relative to the adapter 111.

However, as the adapter 111 moves further toward the gas button 101, an upper face of the button operation member 101a abuts the inclined surface 114a of the extension portion 114 and moves in a direction indicated by arrow B2 while the upper face slides on the inclined surface 114a, that is, the button operation member 101a is pushed in.

Then, as the adapter 111 is moved further in the direction indicated by arrow B1, finally, the flange portion abuts the butting portion 116, providing a state in which the outward flange portion 101c is completely inserted in the groove 115. Upon the outward flange portion 101c being completely inserted in the groove 115, the button operation member 101a is completely pushed in the support member 101b by the flat surface 112a. Also, the button operation member 101a is biased in a direction in which the button operation member 101a is pushed back to the tip portion side, by internal spring pressure. Therefore, upon the adapter 111 being attached to the gas button 101, the button operation member 101a is brought into a depressed state.

Therefore, when the adapter 111 is attached to the gas button 101 and the endoscope 2 is put in the endoscope cleaning apparatus 1 and cleaned/disinfected, a liquid such as a cleaning liquid is supplied also into the gas duct, enabling the inside of the gas duct to be cleaned/disinfected.

Also, in a state in which the outward flange portion 101c is completely inserted in the groove 115, as indicated by the dotted lines in FIG. 20, a liquid such as a cleaning liquid from the sliding apparatus 102 side flows in from a gap between the inside of the adapter 111 and the gas button 101 and passes through the gaps 116a and 116b on the opposite sides of the butting portion 116.

Therefore, when the adapter 111 is attached to the gas button 101 and the endoscope 2 is put in the endoscope cleaning apparatus 1 and cleaned/disinfected, a part of contact between the adapter 111 and the gas button 101 is small, and thus, a liquid such as a cleaning liquid flows smoothly on an outer surface of the gas button 101, enabling the outer surface of the gas button 101 to be sufficiently cleaned/disinfected.

As described above, each of the embodiments described above enables provision of an endoscope connection instrument that can reliably clean and disinfect a fitting part communicably connected to a duct inside an endoscope.

The present invention is not limited to the above-described embodiments, various modifications, alterations and the like are possible without departing from the spirit of the present invention.

What is claimed is:

1. An endoscope connection instrument to be connected to an endoscope fitting, the endoscope connection instrument comprising:
    a first opening having a predetermined outer diameter in order to open inside the endoscope fitting when the endoscope connection instrument is connected to the endoscope fitting;
    a second opening that is communicably connected to the first opening, is arranged on a fluid supply source side relative to the first opening, and allows a fluid from the fluid supply source to flow thereinto via a cleaning tube;
    a hollow portion that is an internal space communicably connected to the first opening and the second opening;
    a cylindrical portion to be inserted into the endoscope fitting, the cylindrical portion covering a part from the first opening to a predetermined position of the hollow portion;
    a narrowing portion to be inserted into the endoscope fitting, the narrowing portion including a side face whose outer diameter increases over a predetermined distance from the predetermined position toward the second opening, and covering the hollow portion; and
    a plurality of grooves formed over a predetermined area from the predetermined position in an outer surface of the narrowing portion.

2. The endoscope connection instrument according to claim 1, wherein a shape of the side face of the narrowing portion is a tapered shape or a bowl shape.

3. The endoscope connection instrument according to claim 1, wherein the plurality of grooves are arranged so as to be symmetrical to each other with reference to a center axis of the narrowing portion.

4. The endoscope connection instrument according to claim 1, wherein each of the plurality of grooves has a fixed depth.

5. The endoscope connection instrument according to claim 1, wherein each of the plurality of grooves is formed along an axis direction of the narrowing portion.

6. The endoscope connection instrument according to claim 2, wherein the shape of the side face is the tapered shape, and a surface of the narrowing portion having the tapered shape is a partial face of a surface shape of a conical shape.

7. The endoscope connection instrument according to claim 2, wherein the shape of the side face is the bowl shape, and a surface of the narrowing portion having the bowl shape is a spherical zone-shaped face.

8. The endoscope connection instrument according to claim 1, further comprising a fitting pressing member including the first opening, the second opening, the hollow portion, the cylindrical portion, the narrowing portion and the plurality of grooves; and
    an elastic member connected to the fitting pressing member.

9. The endoscope connection instrument according to claim 8, further comprising a tube connection portion to which the cleaning tube is to be connected.

10. The endoscope connection instrument according to claim 8, further comprising a cover member covering the fitting pressing member,
   wherein the elastic member is arranged between the fitting pressing member and the cover member, and
   the cover member includes a securing mechanism that secures the endoscope connection instrument to the endoscope fitting when the endoscope connection instrument is attached to the endoscope fitting.

11. The endoscope connection instrument according to claim 1, further comprising a securing member that secures the endoscope connection instrument to the endoscope fitting in a state in which a distal end of the narrowing portion is inserted in the endoscope fitting.

12. An endoscope cleaning/disinfecting apparatus comprising the endoscope connection instrument according to claim 1, the endoscope connection instrument being connected to the endoscope cleaning/disinfecting apparatus via the cleaning tube.

\* \* \* \* \*